(12) United States Patent
Castro et al.

(10) Patent No.: US 7,455,876 B2
(45) Date of Patent: *Nov. 25, 2008

(54) APPARATUS AND METHOD FOR DEPOSITING A COATING ONTO A SURFACE OF A PROSTHESIS

(75) Inventors: Daniel Castro, Santa Clara, CA (US); Steven Wu, Santa Clara, CA (US); Kevin L. Woolbright, Sunnyvale, CA (US); Kurt W. Scheinpflug, Sunnyvale, CA (US); Syed F. A. Hossainy, Fremont, CA (US); Li Chen, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/776,448

(22) Filed: Jul. 11, 2007

(65) Prior Publication Data

US 2008/0014332 A1 Jan. 17, 2008

Related U.S. Application Data

(62) Division of application No. 10/602,487, filed on Jun. 23, 2003, which is a division of application No. 10/043,500, filed on Jan. 10, 2002, now Pat. No. 6,616,765, which is a division of application No. 09/583,371, filed on May 31, 2000, now Pat. No. 6,395,326.

(51) Int. Cl.
*B05D 1/00* (2006.01)
(52) U.S. Cl. .................................. 427/2.24; 427/2.25
(58) Field of Classification Search ................ 427/2.24, 427/2.25
See application file for complete search history.

(56) References Cited

U.S. PATENT DOCUMENTS

| 4,733,665 A | 3/1988 | Palmaz |
| 4,743,252 A | 5/1988 | Martin et al. |
| 4,800,882 A | 1/1989 | Gianturco |
| 4,886,062 A | 12/1989 | Wiktor |

(Continued)

FOREIGN PATENT DOCUMENTS

WO  WO 98/23228  6/1998

OTHER PUBLICATIONS

Impulse Jetting: About Us, http://www.impulsejetting.com/about.html, printed Dec. 18, 2000 (1 page).

(Continued)

*Primary Examiner*—Erma Cameron
(74) *Attorney, Agent, or Firm*—Squire, Sanders & Dempsey L.L.P.

(57) ABSTRACT

A patterned coating on a prosthesis, for example a stent, and a method for forming the coating are disclosed Additionally, an apparatus for forming the patterned coating is disclosed.

40 Claims, 14 Drawing Sheets

U.S. PATENT DOCUMENTS

| | | | |
|---|---|---|---|
| 4,967,606 A | 11/1990 | Wells et al. | |
| 5,015,505 A | 5/1991 | Cetnar | |
| 5,225,750 A | 7/1993 | Higuchi et al. | |
| 5,368,560 A | 11/1994 | Rambo et al. | |
| 5,464,650 A | 11/1995 | Berg et al. | |
| 5,511,726 A | 4/1996 | Greenspan et al. | |
| 5,527,337 A | 6/1996 | Stack et al. | |
| 5,679,400 A * | 10/1997 | Tuch | 427/2.14 |
| 5,700,286 A | 12/1997 | Tartaglia et al. | |
| 5,713,949 A | 2/1998 | Jayaraman | |
| 5,741,554 A | 4/1998 | Tisone | |
| 5,766,710 A | 6/1998 | Turnlund et al. | |
| 5,769,883 A | 6/1998 | Buscemi et al. | |
| 5,824,056 A | 10/1998 | Rosenberg | |
| 5,837,313 A | 11/1998 | Ding et al. | |
| 5,843,172 A | 12/1998 | Yan | |
| 5,869,127 A | 2/1999 | Zhong | |
| 5,873,904 A | 2/1999 | Ragheb et al. | |
| 5,980,972 A | 11/1999 | Ding | |
| 5,984,449 A | 11/1999 | Tajika et al. | |
| 6,056,993 A | 5/2000 | Leidner et al. | |
| 6,096,070 A | 8/2000 | Ragheb et al. | |
| 6,121,027 A | 9/2000 | Clapper et al. | |
| 6,132,809 A | 10/2000 | Hynes et al. | |
| 6,143,370 A | 11/2000 | Panagiotou et al. | |
| 6,209,621 B1 | 4/2001 | Treacy | |
| 6,214,407 B1 | 4/2001 | Laube et al. | |
| 6,224,675 B1 | 5/2001 | Prentice et al. | |
| 6,462,284 B1 | 10/2002 | Hashimoto | |
| 6,491,666 B1 | 12/2002 | Santini, Jr. et al. | |

OTHER PUBLICATIONS

Impulse Jetting: Our Technology, http://www.impulsejetting.com/tech1.html, printed Dec. 18, 2000 (1 page).

Trident, Inc., http://www.tridetintl.com/subbody.html, printed Dec. 18, 2000 (1 page).

Trident, Inc., http://www.tridetintl.com/products-apps/ultrajet.html, printed Dec. 18, 2000 (3 pages).

World Precision Instruments, Inc., "Nanolite Injector," http://www.wpiinc.com/WPI_Web/Microinjection/Nanoliter_Injector.html, printed Sep. 18, 2003 (2 pages).

World Precision Instruments, Inc., "Pneumatic PicoPumps," httm://www.wpi-europe.com/pumps/Pneumatic_PicoPumps.html, printed Sep. 18, 2003 (5 pages).

http://www.wpiinc.com/WPI_Web/Pumps/pneumatic_Fig.gif, printed Sep. 30, 2002 (1 page).

World Precision Instruments, Inc., "Pneumatic PicoPumps," http://www.wpiinc.com/WPI_Web/Microinjection/Pneumatic_PicoPumps.html, printed Sep. 18, 2003 (4 pages).

World Precision Instruments, Inc., "Nanoliter 2000," http://www.wpi-europe.com/pumps/Nanoliter_Injector.html, printed Sep. 18, 2003 (3 pages).

* cited by examiner

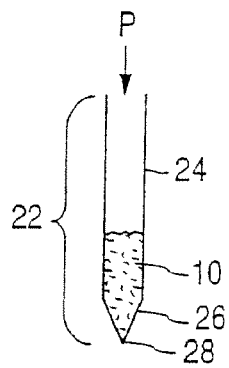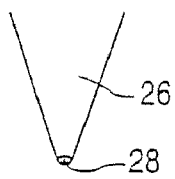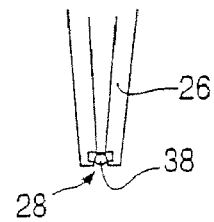
Figure 3A  Figure 3B  Figure 3C
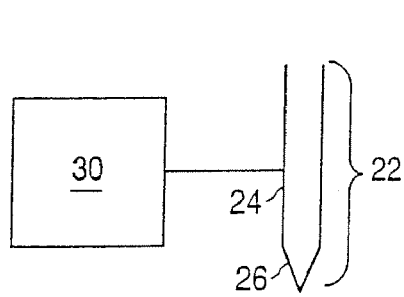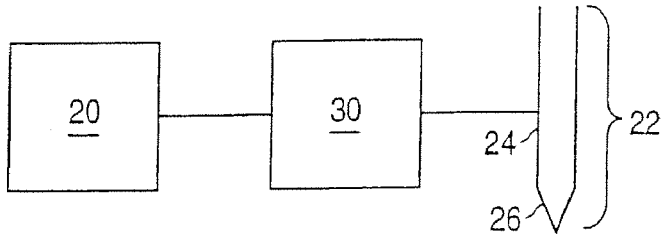
Figure 3D  Figure 3E
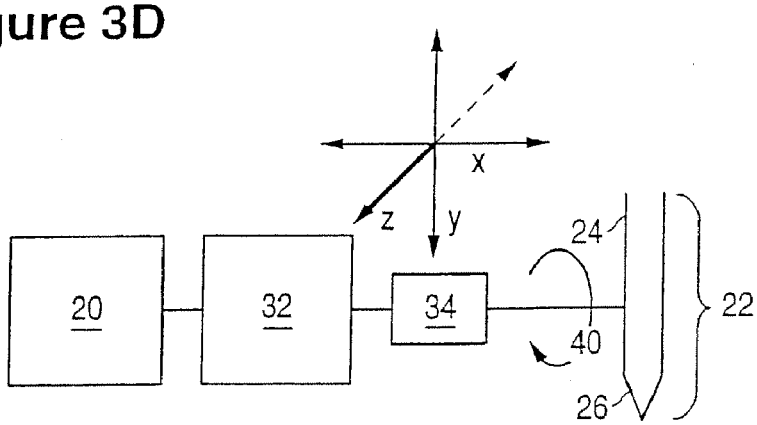
Figure 3F
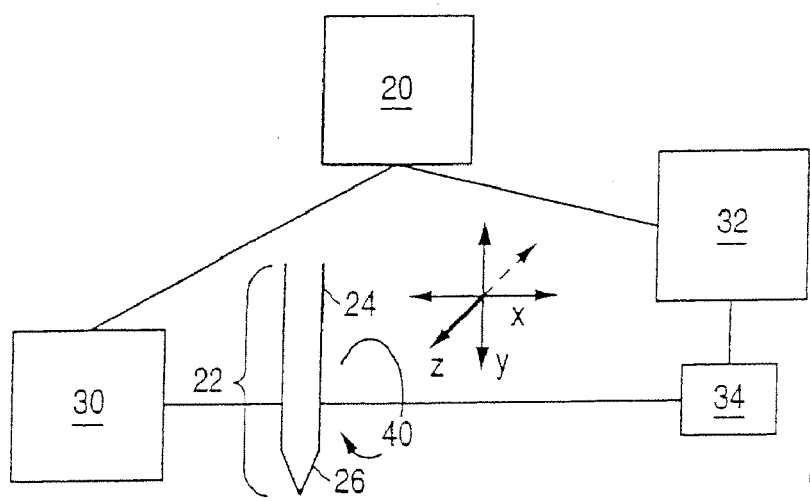
Figure 3G

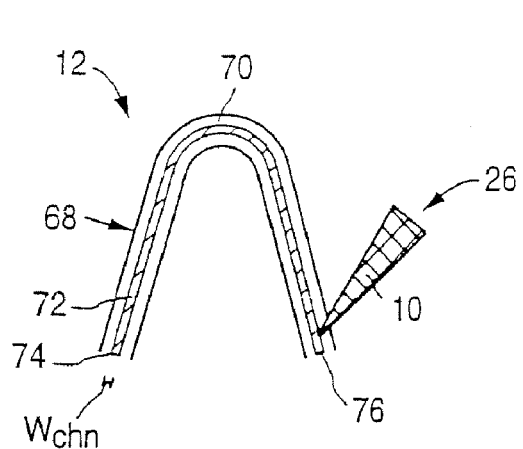
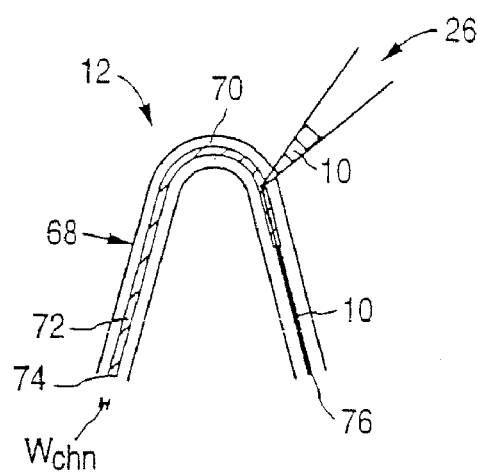
Figure 9A        Figure 9B
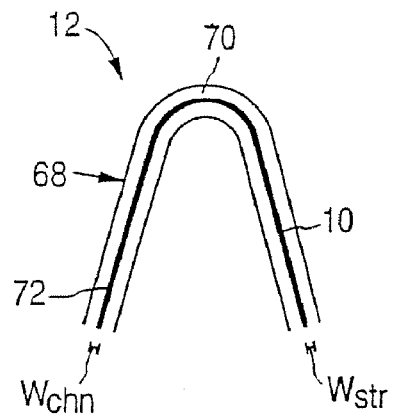
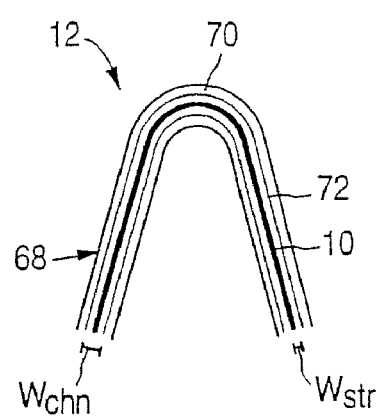
Figure 10A       Figure 10B
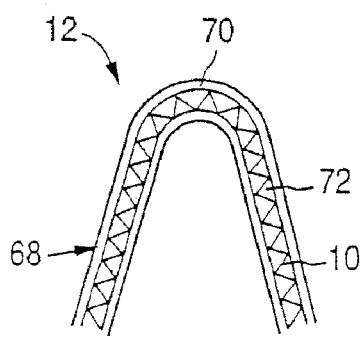
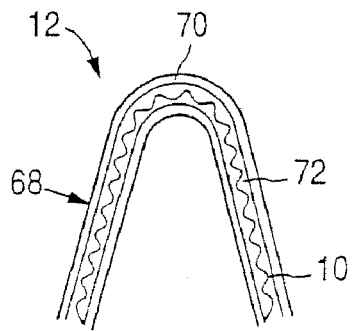
Figure 10C       Figure 10D

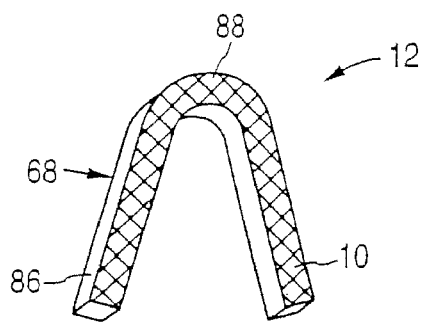
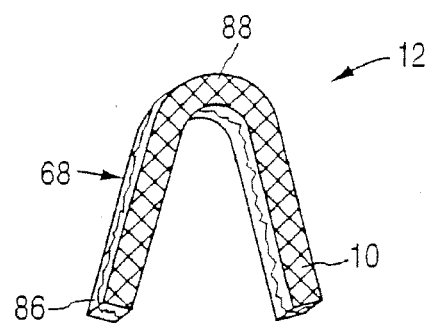
Figure 15A                    Figure 15B
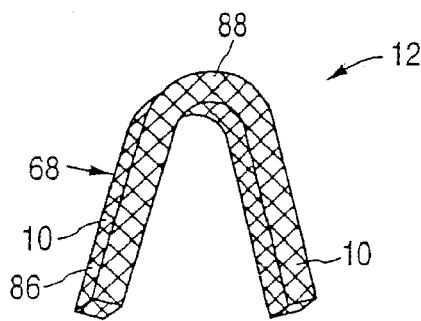
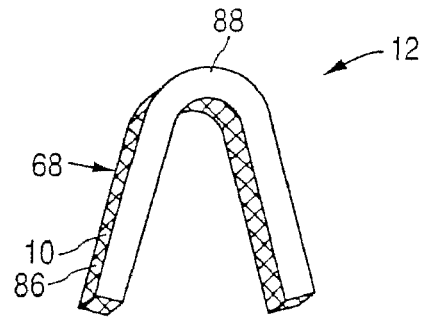
Figure 15C                    Figure 15D
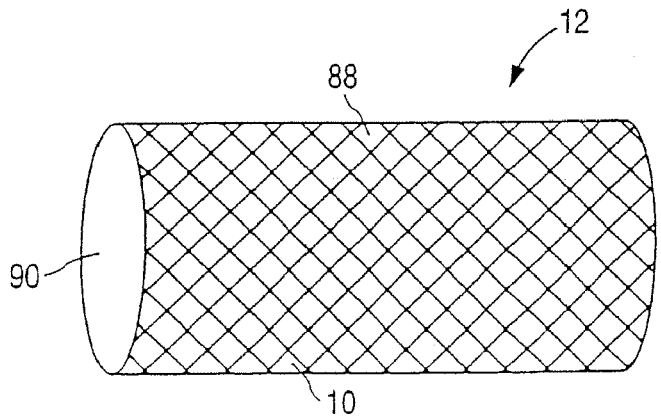
Figure 16A
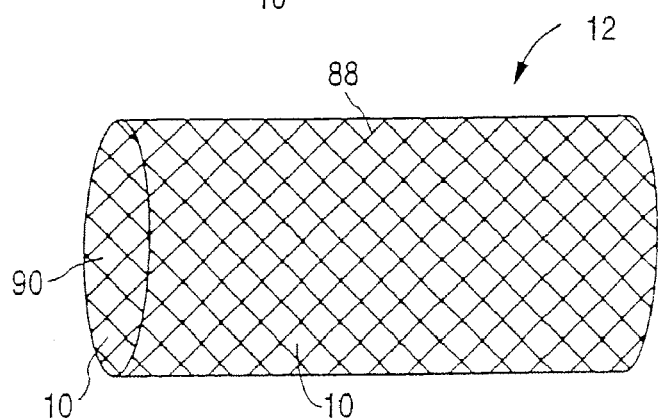
Figure 16B окажу# APPARATUS AND METHOD FOR DEPOSITING A COATING ONTO A SURFACE OF A PROSTHESIS This application is a divisional application of U.S. patent application Ser. No. 10/602,487, filed Jun. 23, 2003, which is a divisional application of U.S. patent application Ser. No. 10/043,500, filed Jan. 10, 2002, now U.S. Pat. No. 6,616,765, which is a divisional application of U.S. patent application Ser. No. 09/583,371, filed May 31, 2000, now U.S. Pat. No. 6,395,326. The entire disclosures of these applications are incorporated here in by reference.

BACKGROUND OF THE INVENTION

1. Field of the Invention

This invention relates generally to implantable devices, such as an expandable intraluminial prosthesis, one example of which includes a stent. More particularly, the invention is directed to an apparatus and method for coating a prosthesis.

2. Description of the Related Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion against the inner wall of the artery to dilate the lumen. The balloon is deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, an expandable intraluminal prosthesis, one example of which includes a stent, is implanted in the lumen to maintain the vascular patency. Stents are scaffoldings, usually cylindrical or tubular in shape, which function to physically hold open and, if desired, to expand the wall of the passageway. Typically stents are capable of being compressed for insertion through small cavities via small catheters, and expanded to a larger diameter once at the desired location. Examples in patent literature disclosing stents which have been successfully applied in PTCA procedures include U.S. Pat. No. 4,733,665 issued to Palmaz, U.S. Pat. No. 4,800,882 issued to Gianturco, and U.S. Pat. No. 4,886,062 issued to Wiktor.

To treat the damaged vasculature tissue and assist prevention of thrombosis and restenosis, there is a need for administrating therapeutic substances to the treatment site. For example, anticoagulants, antiplatelets and cytostatic agents are commonly used to prevent thrombosis of the coronary lumen, to inhibit development of restenosis, and to reduce post-angioplasty proliferation of the vascular tissue, respectively. To provide an efficacious concentration to the treated site, systemic administration of such medication often produces adverse or toxic side effects for the patient. Local delivery is a preferred method of treatment in that smaller total levels of medication are administered at a specific site in comparison to larger overall dosages that are applied systemically. Local delivery produces fewer side effects and achieves more effective results.

One commonly applied technique for the local delivery of a drug is through the use of a polymeric carrier coated onto the surface of a stent, as disclosed in U.S. Pat. No. 5,464,650 issued to Berg et al. Berg disclosed applying to a stent body a solution which included a specified solvent, a specified polymer dissolved in the solvent, and a therapeutic substance dispersed in the blend. The solvent was allowed to evaporate, leaving on the stent surface a coating of the polymer and the therapeutic substance impregnated in the polymer. As indicated by Berg, stents were immersed in the solution 12 to 15 times or sprayed 20 times.

The immersion method of coating a stent, also called dip-coating, entails submerging the entire stent, or an entire section of the stent, in a polymer solution. Similarly, spray-coating requires enveloping the entire stent, or an entire section of the stent, in a large cloud of polymeric material. One disadvantage of dip-coating and spray-coating methods is the inability to control the exact geometrical pattern of coating on the stent or section of the stent. Another shortcoming of both dip- and spray-coating is the possibility of forming web-like defects by build-up of excess polymeric material within the radii of the stent. Web-like defects are most prevalent in stents having tight patterns, for example coronary stents, such that the radii are very small.

Another disadvantage of both dip-coating and spray-coating stems from a low-viscosity requirement for the polymer solution in which the stent is dipped or with which the stent is sprayed. A low viscosity solution can only be achieved by using a low molecular weight polymer or by using a very low concentration of polymer in the polymer solution. Thus, both dip-coating and spray-coating methods have imposed limitations in type and concentration of applied polymers.

Other commonly applied techniques for coating a stent with a polymeric material include sputtering and gas phase polymerization. Sputtering typically involves placing a polymeric coating material target in an environment, and applying energy to the environment that hits the target and causes emission of polymeric material from the target. The polymeric emissions deposit onto the stent, forming a coating. Similarly, gas phase polymerization typically entails applying energy to a monomer in the gas phase within a system set up such that the polymer formed is attracted to a stent, thereby creating a coating around the stent.

Sputtering and gas phase polymerization have similar shortcomings. Like the dip-coating and spray-coating techniques, the sputtering and gas phase polymerization techniques do not allow control of the geometrical pattern in which the stent will be coated and are quite limited in the selection of polymers that can be employed. In addition, coating a stent with a polymer and a drug at the same time via sputtering or gas phase polymerization has not been demonstrated to be effective and risks degradation of the drug. Moreover, techniques for applying a polymeric coating by sputtering or gas phase polymerization and later incorporating a drug into the applied polymeric coating are limited.

Accordingly, it is desirable to provide an improved method of applying a polymeric coating to a prosthesis. Specifically, it is desirable to provide a method of applying a polymeric coating to a prosthesis which enables control over the geometrical pattern in which a prosthesis is coated, reduces the incidence of web-like defects due to excess build-up of polymeric material, broadens the field of both the types and the concentrations of polymers which may be used to coat a prosthesis, and allows a prosthesis to be coated with a polymer and a drug at the same time.

SUMMARY OF THE INVENTION

In accordance with one embodiment of the present invention, a method of forming a coating onto a surface of a prosthesis, such as a stent, is provided. The method comprises providing a composition and depositing the composition in a preselected geometrical pattern onto a first surface of the prosthesis to form the coating.

In one embodiment, the method comprises providing a composition that includes a polymer and a solvent. The polymer can constitute from about 0.1% to about 25% by weight of the total weight of the composition and the solvent can constitute from about 75% to about 99.9% by weight of the total weight of the composition.

In accordance with another embodiment, sufficient amounts of a therapeutic substance or a combination of substances are included in the composition of the polymer and the solvent. In this embodiment, the polymer can constitute from about 0.1% to about 25% by weight of the total weight of the composition. The solvent can constitute from about 49.9% to about 99.8% by weight of the total weight of the composition. The therapeutic substance can constitute from about 0.1% to about 50% by weight of the total weight of the composition.

In accordance with other embodiments, the method comprises providing a composition that includes a monomer. A monomeric composition may also include a solvent and/or a therapeutic substance. The monomeric composition may be cured to form a polymeric coating.

In accordance with other embodiments, the method comprises providing a composition that includes a polymer without a solvent. The composition may also include a therapeutic substance. The composition may be heated prior to being deposited onto the prosthesis.

In accordance with other embodiments, the method comprises providing a composition that includes a therapeutic substance. The composition may also include a solvent.

In accordance with one embodiment, depositing the composition in a preselected geometrical pattern comprises moving a dispenser assembly along a predetermined path while depositing the composition onto a stationary prosthesis. In accordance with another embodiment, depositing the composition in a preselected geometrical pattern comprises moving a holder assembly supporting the prosthesis along a predetermined path while a stationary dispenser assembly deposits the composition onto the prosthesis. In accordance with still another embodiment, depositing the composition in a preselected geometrical pattern comprises moving a holder assembly supporting the prosthesis along a first predetermined path and moving a dispenser assembly along a second predetermined path.

The preselected geometrical pattern of the composition as deposited onto a surface of the prosthesis may be a continuous stream that is either in a substantially straight line or a line that has a curved or angular pattern. The preselected geometrical pattern may also be an intermittent pattern that is in a straight line, a line that is curved or angular, or includes at least one bead.

In accordance with some embodiments, the prosthesis contains a channel extending from a first position along the first surface to a second position along the first surface and within which the composition is at least partially deposited. The preselected geometrical pattern of the composition as deposited within a channel of the prosthesis may be a continuous stream that is in a straight line or a non-straight line such as a curved line or angular line. The preselected geometrical pattern may also be an intermittent pattern that is in a straight line, a non-straight line such as a curved line or angular line, or includes at least one bead.

In accordance with other embodiments, the prosthesis contains a first cavity within the first surface of the prosthesis within which the composition is at least partially deposited. The predetermined geometrical pattern may be a bead.

In some embodiments, the application of the composition to the prosthesis is followed by the redistribution of the composition along the prosthesis. Redistribution of the composition may be accomplished by using, for example, air pressure, centrifugal force, or a second solvent.

The polymer, with or without the therapeutic substance, solidifies and adheres to the prosthesis following removal of the solvent to substantial elimination.

In accordance with another embodiment of the invention, an apparatus for depositing a composition onto a surface of a prosthesis is provided. The apparatus comprises a dispenser assembly having a nozzle for depositing a composition onto a surface of a prosthesis, a holder assembly for supporting a prosthesis, and a motion control system for either moving the dispenser assembly along a predetermined path or moving the holder assembly along a predetermined path.

The dispenser assembly may deposit the composition in a preselected geometrical pattern onto a surface of the prosthesis, at least partially within a channel formed into the prosthesis or at least partially within one or more cavities formed into the prosthesis. The preselected geometrical pattern of the deposited composition may be a continuous stream that is in a straight line or a non-straight line such as a curved line or angular line. The preselected geometrical pattern may also be an intermittent pattern that is in a straight line, a non-straight line such as a curved line or angular line, or includes at least one bead.

In accordance with some embodiments, the dispenser assembly can deposit a second composition in a preselected geometrical pattern onto the prosthesis. The first and second compositions may be in contact with one another in at least one location on the prosthesis.

In some embodiments, the dispenser assembly has a nozzle having an orifice with an orifice diameter in the range of approximately 0.5 microns to approximately 150 microns. In other embodiments, the nozzle has an orifice that can capture a last droplet of the composition to prevent lifting of the last droplet from the prosthesis. In other embodiments, the nozzle can be positioned at a 90° angle with respect to the prosthesis during deposition of the composition. In still other embodiments, the nozzle can be positioned at an angle less than 90° with respect to the prosthesis during deposition of the composition. In other embodiments, the dispenser assembly has more than one nozzle.

In accordance with some embodiments, the dispenser assembly is coupled to a delivery control system. The delivery control system may be in communication with a CPU.

In accordance with some embodiments, the motion control system is for moving the dispenser assembly along a predetermined path. The motion control system may be in communication with a CPU and may move the dispenser assembly along a predetermined path in the x, y, z, and/or rotational directions.

In accordance with other embodiments, the motion control system is for moving the holder assembly along a predetermined path. The motion control system may be in communication with a CPU and may move the holder assembly along a predetermined path in the x, y, z, and/or rotational directions.

In accordance with other embodiments, a first motion control system is for moving the dispenser assembly along a first predetermined path and a second motion control system is for moving the holder assembly along a second predetermined path.

In accordance with some embodiments, the apparatus additionally includes a feedback system. The feedback system includes a video camera for capturing an image, a lens system coupled to the video camera, frame grabber hardware to accept the image, and vision software to characterize the image. Image data from the video camera is fed back to the motion control system, the dispenser assembly, and/or the holder assembly to direct deposition of the composition onto the surface of the prosthesis.

BRIEF DESCRIPTION OF THE FIGURES

FIG. 3A illustrates a dispenser assembly that is suitable for usage in depositing a coating on a prosthesis.

FIGS. 3B and 3C illustrate examples of a nozzle of a dispenser assembly.

FIGS. 3D and 3E illustrate examples of a dispenser assembly having a delivery control system.

FIG. 3F illustrates a dispenser assembly having motion capabilities.

FIG. 3G illustrates a dispenser assembly having a delivery control system as well as motion capabilities.

FIGS. 9A and 9B illustrate the application of the composition into a channel within a strut.

FIG. 10A illustrates a strut having a coating that completely fills a channel within the strut.

FIG. 10B illustrates a strut having a continuous stream of coating that is in a straight line in a channel within the strut.

FIG. 10C illustrates an example of a strut having a continuous stream of coating that is applied in an angular line in a channel within the strut.

FIG. 10D illustrates an example of a strut having a continuous stream of coating that is applied in a curved line in a channel within the strut.

FIGS. 15A, 15B, and, 15C illustrate the redistribution of the composition along a portion of the prosthesis.

FIG. 15D illustrates a portion of a prosthesis upon which the composition has been redistributed.

FIGS. 16A and 16B illustrate redistribution of the composition along the prosthesis.

DETAILED DESCRIPTION OF THE EMBODIMENTS

Apparatus for Depositing a Composition onto a Prosthesis

Figure 1:
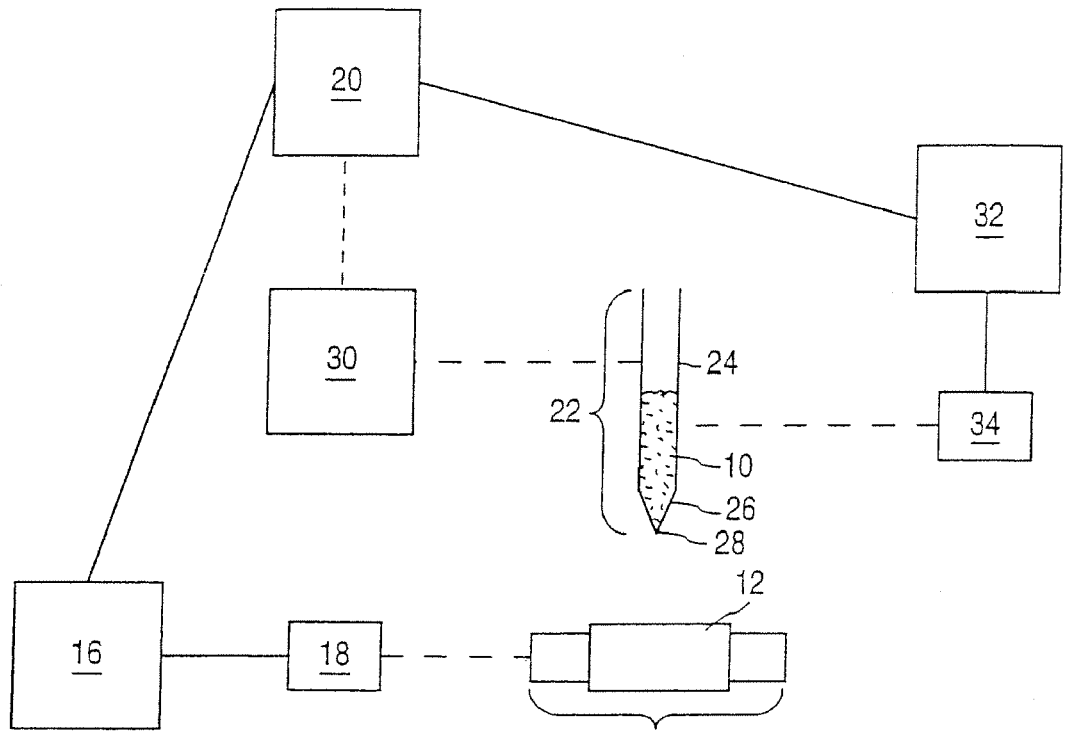
FIG. 1 illustrates a typical set-up of components which may be used to form a coating onto a surface of a prosthesis according to an aspect of the present invention.

Referring now to the drawings, wherein similar parts are identified by like reference numerals, FIG. 1 illustrates the various components which may be involved in the deposition of a composition 10 onto a surface of a prosthesis 12 in accordance with an aspect of the present invention. A broken line between two components in FIG. 1 represents an optional coupling which is present in some, but not all, embodiments of the deposition method. Prosthesis 12 is supported in a holder assembly 14 which may be coupled to a holder motion control system 16 through a holder driving component 18. Holder motion control system 16 is in communication with CPU 20. A dispenser assembly 22 includes a reservoir 24 and a nozzle 26 having an orifice 28. Dispenser assembly 22 may be coupled to a delivery control system 30 which can be in communication with CPU 20. Dispenser assembly 22 may also be coupled to a dispenser motion control system 32 through a dispenser driving component 34. Dispenser motion control system 32 is in communication with CPU 20.

Prosthesis 12 may be any suitable prosthesis, examples of which include self-expandable stents and balloon-expandable stents. Prosthesis 12 can be in an expanded or unexpanded state during processing according to the disclosed method. The underlying structure of prosthesis 12 can be virtually of any design. Prosthesis 12 can be made of a metallic material or an alloy such as, but not limited to, stainless steel, "MP35N," "MP20N," elastinite (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Prosthesis 12 made from bioabsorbable or biostable polymers could also be used with composition 10. A polymeric prosthesis 12 should be compatible with composition 10. Further, in some embodiments, prosthesis 12 may include one or more channels and/or cavities formed therein.

In one embodiment, prosthesis 12 is a stent which includes a single cavity, or a plurality of cavities, formed therein. A cavity, which may also be referred to as a pore or a depot, may be formed as a laser trench on a stent by exposing the surface to an energy discharge from a laser, such as an excimer laser. Alternative methods of forming such cavities include, but are not limited to, physical and chemical etching techniques. Techniques of laser fabrication or etching to form cavities are well-known to one of ordinary skill in the art. Cavities can be formed in virtually any stent structure. Cavities are formed by a manufacturer at any preselected location and have any preselected depth, size, and geometrical configuration. The location of a cavity or cavities within a stent varies according to intended usage and application. The depth and size of a cavity typically depend on the material and dimensions of the stent and the type and amount of substances deposited within the cavity as well as on the clinical purpose and usage of the stent. The depth and size of the individual cavities formed on a single stent can vary relative to one another. Cavities may be formed in a variety of selected geometrical shapes including, but not limited to, generally cylindrical shapes, generally conical shapes, and elongated trenches.

Figure 2A:
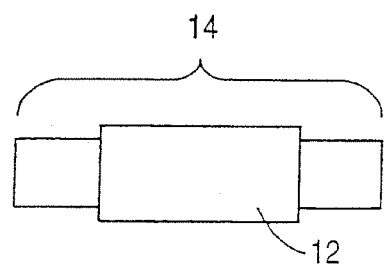
FIG. 2A illustrates a prosthesis supported by a holder assembly according to another aspect of the present invention.
Figure 2B:
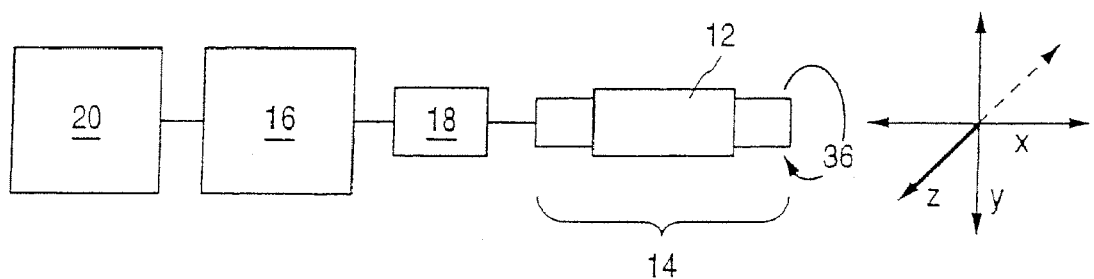
FIG. 2B illustrates a holder assembly having motion capabilities.

As shown in FIG. 2A, holder assembly 14 is used to support the above-described prosthesis 12 during deposition. A suitable holder assembly 14 allows access to the entire top surface, i.e., tissue-contacting surface, of prosthesis 12 while holding prosthesis 12 securely and without damaging prosthesis 12. In addition, a suitable holder assembly 14 is capable of being coupled to and controlled by holder motion control system 16, for example holder assembly 14 illustrated in FIG. 2B.

Holder motion control system 16 may be any suitable holder motion control system 16 coupled to holder assembly 14 through holder driving component 18 and communicating with CPU 20. Holder motion control system 16 controls the motion of holder assembly 14 in response to commands from CPU 20. Holder motion control system 16 should have the capability of maneuvering holder driving component 18 in the x, y, and z directions as well as providing rotational motion as indicated by arrow 36. Holder motion control system 16 should have the capabilities of moving holder driving component 18 from a stopped position at intervals of less than 0.001 inch. Additionally, holder motion control system 16 should be capable of terminating the motion of holder driving component 18 at less than 0.001 inch from the position at which a termination signal from CPU 20 is received. Holder motion control system 16 must also be capable of following a given pattern on prosthesis 12 as selected by the user via CPU 20.

Dispenser assembly 22 is used for a controlled delivery and deposition of composition 10 on prosthesis 12. As shown in FIG. 3A, dispenser assembly 22 can be a simple device consisting only of reservoir 24 which holds composition 10 prior to delivery and nozzle 26 having orifice 28 through which composition 10 is delivered. One exemplary type of dispenser assembly 22 can be an ink-jet printhead. Another exemplary type of dispenser assembly 22 can be a microinjector capable of injecting small volumes ranging from about 2 to about 70 nL, such as NanoLiter 2000 available from World Precision Instruments or Pneumatic PicoPumps PV830 with Micropipette available from Cell Technology System. Such microinjection syringes may be employed in conjunction with a microscope of suitable design.

Nozzle 26 may be permanently affixed to reservoir 24, removable, or disposable. Nozzle 26 may be of any suitable material including, but not limited to, glass, metal, sapphire, and plastics. Particular care should be taken to ensure that a glass nozzle 26 does not make contact with prosthesis 12 upon deposition of composition 10 to avoid nozzle 26 breakage. Particular care should also be taken to ensure that a plastic nozzle 26 is compatible with components of composition 10. Nozzle 26 may be of any suitable design including, but not limited to the designs of FIGS. 3B and 3C. Nozzle 26 depicted in FIG. 3C may be particularly useful for applications in which lifting of a final droplet 38 of composition 10 is undesirable, as the depicted design of nozzle 26 allows the capture of final droplet 38 within orifice 28. In addition, dispenser assembly 22 may include more than one nozzle 26.

Orifice 28 of nozzle 26 can range in diameter from about 0.5 μm to about 150 μm. The particular size of orifice 28 depends on factors such as the constituents of composition 10, the viscosity of composition 10 to be applied, the deposition pattern that is desired, and the type of prosthesis 12 employed. For example, a larger orifice 28 may be utilized for application of composition 10 to the entire outer surface of prosthesis 12 than the orifice 28 for the application of composition 10 into discrete channels or cavities within prosthesis 12.

Delivery of composition 10 using dispenser assembly 22 can be achieved either passively or actively. Delivery can be achieved passively via capillary action. Alternatively, delivery can be achieved actively by applying a pressure p to composition 10 in reservoir 24 as depicted in FIG. 3A. Air pressure may be employed to apply pressure p. Continuous air pressure is applied if deposition of a continuous stream of composition 10 is desired. Bursts of air pressure can be employed if an intermittent deposition pattern of composition 10 is desired. Active delivery may also be achieved via acoustic, ultrasonic, fluid, or any other forms of pressure known and available to one of ordinary skill in the art.

In one embodiment, delivery control system 30 is coupled to dispenser assembly 22 as depicted in FIG. 3D. Operating parameters such as the timing, volume, and speed of both filling and delivery as well as the pressure applied may be controlled via delivery control system 30. Operation of delivery control system 30 may be accomplished manually by the user. Alternatively, operation of delivery control system 30 may be accomplished via CPU 20 in communication with delivery control system 30 as shown in FIG. 3E.

In another embodiment, dispenser motion control system 32 provides dispenser assembly 22 with the capability of motion as shown in FIG. 3F. Dispenser motion control system 32 maybe any suitable dispenser motion control system 32 coupled to dispenser assembly 22 through dispenser driving component 34 and communicating with CPU 20. Dispenser motion control system 32 controls the motion of dispenser assembly 22 in response to commands from CPU 20. Dispenser motion control system 32 should have the capability of maneuvering dispenser driving component 34 in the x, y, and z directions as well as providing rotational motion as indicated by arrow 40. Dispenser motion control system 32 should have the capabilities of moving dispenser driving component 34 from a stopped position at intervals of less than 0.001 inch. Additionally, dispenser motion control system 32 should be capable of terminating the motion of dispenser driving component 34 at less than 0.001 inch, from the position at which a termination signal from CPU 20 is received. Dispenser motion control system 32 must also be capable of following a given pattern on prosthesis 12 as selected by the user via CPU 20.

In another embodiment depicted in FIG. 3G, dispenser assembly 22 is coupled to both delivery control system 30 and dispenser motion control system 32. Thus in this embodiment, dispenser assembly 22 is capable of precise filling and delivery as well as motion in the x, y, and z directions and rotation in the direction of arrow 40.

Figure 4A:
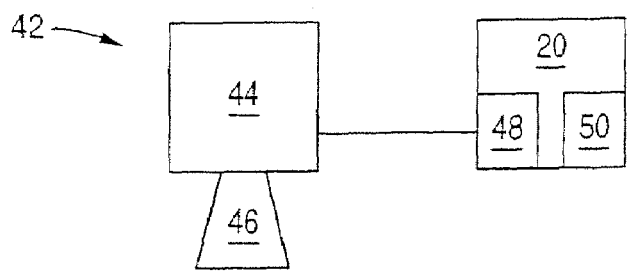
FIG. 4A illustrates an exemplary feedback system that is suitable for usage in controlling the dispenser assembly.

In some embodiments of the invention, a feedback system 42 directs the deposition pattern of composition 10 onto prosthesis 12. FIG. 4A illustrates an exemplary feedback system 42. Feedback system 42 includes a video camera 44 and a lens system 46 as well as frame grabber hardware 48 and vision software 50 within CPU 20.

Video camera 44 may be a standard charge coupled device (CCD) video camera. Video camera 44 should be of high quality. Lens system 46 is typically a set of high quality magnifying video camera lenses having a magnification of at least 1×, usefully in the range from about 3× to about 25×. Lens system 46 may have set optics or utilize a zoom lens. A zoom lens is particularly useful in applications in which a single lens system 46 is used to view images of varying sizes.

Frame grabber hardware 48 may be a PCI (peripheral channel interface) card. Suitable frame grabber hardware 48 should be capable of at least 256 discrete gray levels. Further, frame grabber hardware 48 should be capable of single frame acquisition as well as up to about 30 frames/second real time acquisition.

Vision software 50 may be Active X technology which allows vision programming across a Windows NT platform. Active X tools which may be used in the present invention include, but are not limited to, line caliper tools which measure width, edge tools which locate edges, image calculator tools which determine the difference between multiple images, and blob analysis tools which measure, quantitate and compare irregular shapes. Suitable vision software 50 should be compatible with Visual Basic or C++. Representative examples of suitable vision software 50 include XCaliper by FSI Automation, formerly by Optimus Corporation, and Cognex by Cognex Corporation.

In operation, video camera 44 and lens system 46 capture an image in real time. The captured image may be of, for example, an individual strut, a particular characteristic of a prosthesis, a unique pattern on a prosthesis, or the position of a nozzle relative to a particular location on a prosthesis. Frame grabber hardware 48 accepts the captured image either as a moving video or as a single, still frame and places the video or frame into a format which can be utilized by vision software 50. Vision software 50 measures, adjusts, and otherwise characterizes the image and converts the data into a form that can be sent as feedback to and understood by, for example, delivery control system 30, holder motion control system 16, or dispenser motion control system 32.

Figure 4B:
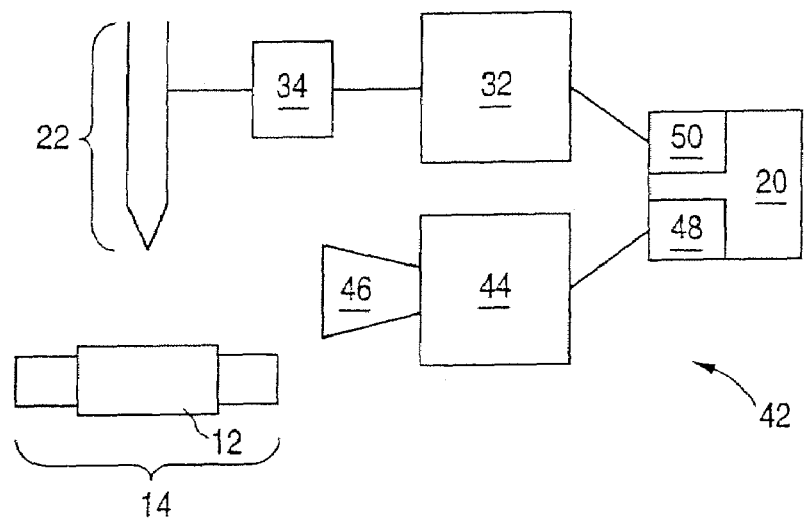
FIG. 4B illustrates a feedback system capable of controlling the motion of a dispenser assembly.

In one embodiment, feedback system 42 controls the deposition pattern of composition 10 on prosthesis 12 by controlling the motion of dispenser assembly 22. In this embodiment, feedback system 42 can assess the relative locations of nozzle 26 of dispenser assembly 22 as well as of particular features of prosthesis 12 and provide feedback via CPU 20 to dispenser motion control system 32 which directs the motion of dispenser assembly 22, as depicted in FIG. 4B.

Figure 4C:
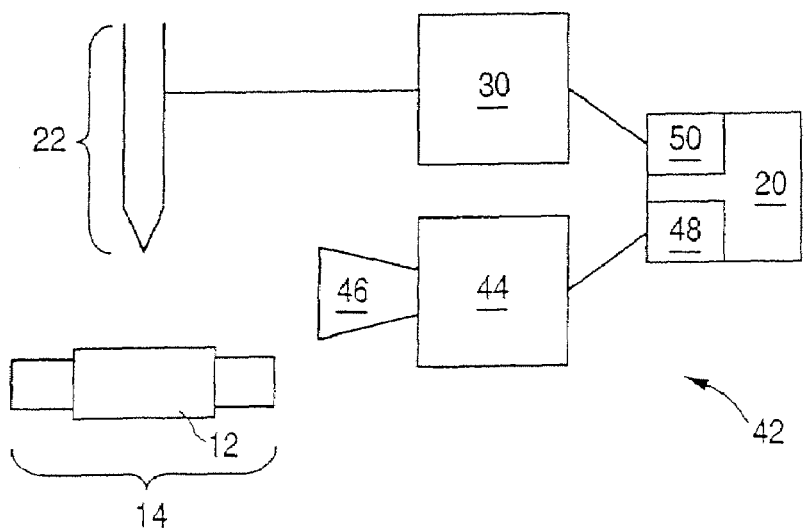
FIG. 4C illustrates a feedback system capable of controlling delivery of the composition from a dispenser assembly.

In an alternative embodiment, feedback system 42 controls the deposition pattern of composition 10 on prosthesis 12 by controlling the delivery of composition 10 from dispenser assembly 22. In this embodiment, feedback system 42 can assess the relative locations of nozzle 26 of dispenser assembly 22 as well as of particular features of prosthesis 12 and provide feedback via CPU 20 to delivery control system 30 which directs the delivery of composition 10 from dispenser assembly 22 onto prosthesis 12, as depicted in FIG. 4C.

Figure 4D:
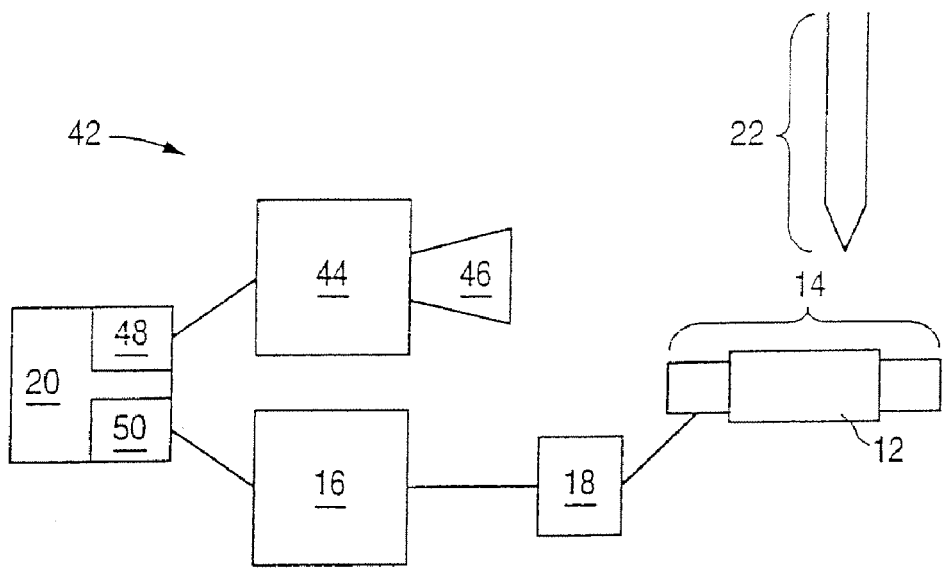
FIG. 4D illustrates a feedback system capable of controlling the motion of a holder assembly.

In still another embodiment, feedback system 42 controls the deposition pattern of composition 10 onto prosthesis 12 by providing feedback via CPU 20 to holder motion control system 16 which directs the motion of holder assembly 14 supporting prosthesis 12, as depicted in FIG. 4D.

Figures 5A, 5B:
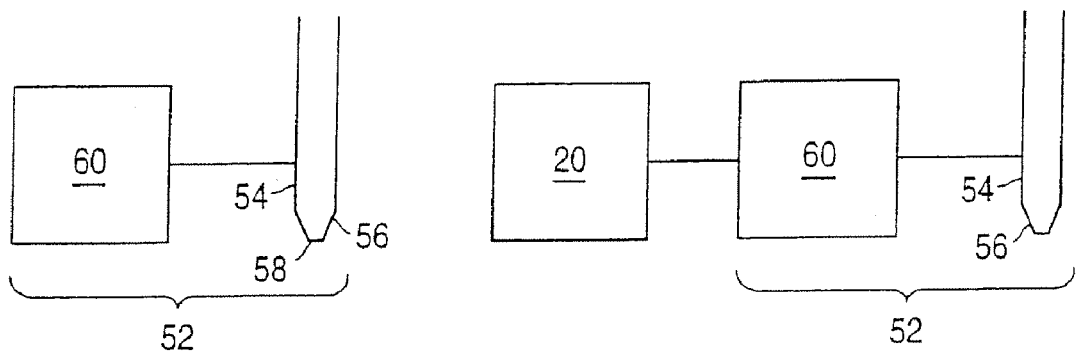
FIGS. 5A and 5B illustrate examples of a heating assembly suitable for usage in drying or curing a coating on a prosthesis.

In some embodiments, a heating assembly 52 is used for controlled drying and/or curing of a coating on prosthesis 12. As shown in FIG. 5A, heating assembly 52 can be a device including a heat conduit 54, a heating nozzle 56 having an orifice 58 through which heat is delivered, and a heating control system 60.

Heat conduit 54 delivers heat from heating control system 60 to heating nozzle 56. Heat conduit 54 may be permanently affixed to heating control system 60 or removable. Heat conduit 54 maybe of any suitable material including, but not limited to, metal, glass, and high-temperature plastic. Particular care should be taken to ensure that the material of which heat conduit 54 is made is heat-resistant.

Heating nozzle 56 may be permanently affixed to heat conduit 54, removable, or disposable. Heating nozzle 56 may be of any suitable material including, but not limited to, metal, glass, and high-temperature plastic. Particular care should be taken to ensure that a glass heating nozzle 56 does not make contact with prosthesis 12 upon heating to avoid heating nozzle 56 breakage. Particular care should also be taken to ensure that heating nozzle 56 is heat-resistant. In addition, heating nozzle 56 may be of any suitable shape or design.

Orifice 58 of heating nozzle 56 can range in diameter from about 50 μm to about 300 μm. The particular size of orifice 58 depends on factors such as the geometries of the struts as well as the geometries of the channels and/or cavities within the struts. For example, a larger orifice 58 may be utilized for application of heat to the entire outer surface of prosthesis 12 than the orifice 58 for the application of heat over discrete channels or cavities within prosthesis 12.

Heating control system 60 may function as both a heat source and a controller of operating parameters such as the timing and temperature of heating. Operation of heating control system 60 may be accomplished manually by the user. Alternatively, operation of heating control system 60 may be accomplished via CPU 20 in communication with heating control system 60 as shown in FIG. 5B. In another embodiment, heating control system 60 is contained within delivery control system 30 described above, such that both the deposition and the heating of a composition is controlled by a single component.

Figure 5C:
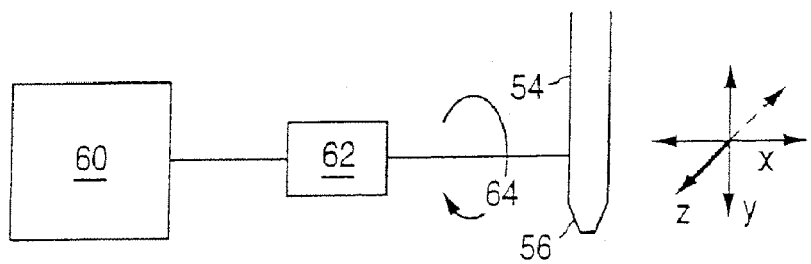
FIGS. 5C, 5D, and 5E illustrate examples of a heating assembly having motion capabilities.

In some embodiments, heat conduit 54 and thus heating nozzle 56 have automated motion capabilities. In one such embodiment, heating control system 60 provides heat conduit 54 and heating nozzle 56 with the capability of motion, as shown in FIG. 5C. Through a heater driving component 62, heat conduit 54 and heating nozzle 56 may be capable of motion in the x, y, and z directions and rotation in the direction of arrow 64 and may also be capable of following a given pattern on prosthesis 12 as selected by the user.

Figure 5D:
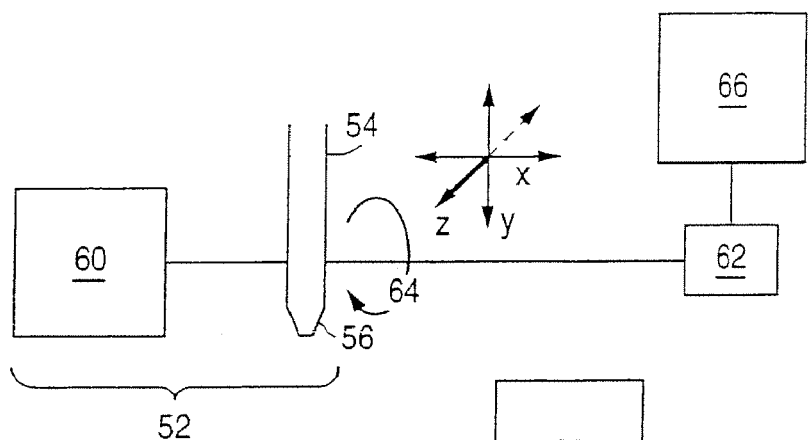
Figure 5E:
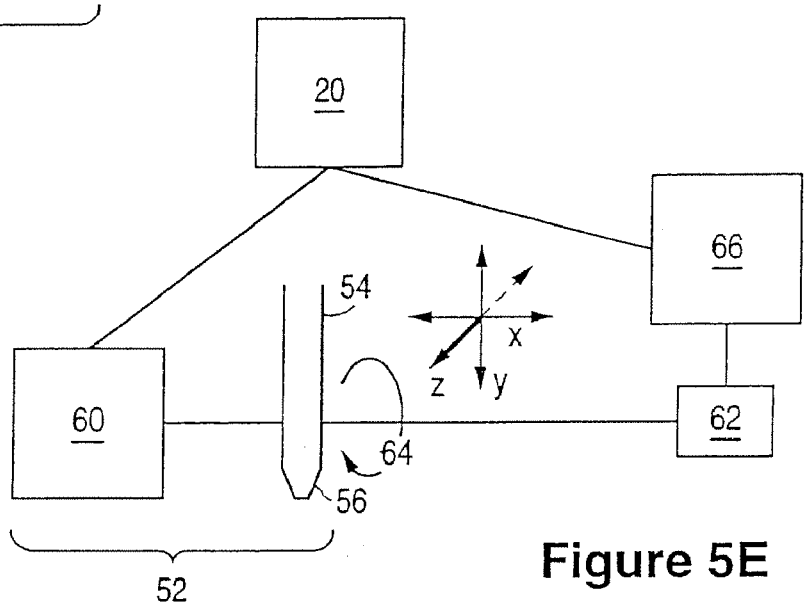

In an alternative embodiment depicted in FIG. 5D, a separate heating motion control system 66 provides heat conduit 54, and thus heating nozzle 56, with the capability of motion. Heating motion control system 66 may be any suitable heating motion control system 66 coupled to heating assembly 52 through heater driving component 62. Heating motion control system 66 may be in communication with CPU 20, such that heating motion control system 66 controls the motion of heat conduit 54 and heating nozzle 56 in response to commands from CPU 20 as shown in FIG. 5E. In such embodiments, heat conduit 54 and heating nozzle 56 may be capable of motion in the x, y, and z directions and rotation in the direction of arrow 40 and may also be capable of following a given pattern on prosthesis 12 as selected by the user. In still another embodiment, heating motion control system 66 is contained within dispenser motion control system 32 described above, such that the motions of both dispenser assembly 22 and heating assembly 52 are controlled by a single component.

In yet another embodiment, feedback system 42 directs the application of heat by heating assembly 52 to composition 10 along the preselected geometrical pattern in which composition 10 was deposited.

Composition

Composition 10 to be deposited onto prosthesis 12 is prepared by conventional methods wherein all components are combined and blended. More particularly, in accordance with one example, a predetermined amount of a polymer is added to a predetermined amount of a solvent. The addition of polymer may be conducted at ambient pressure and under anhydrous atmosphere. If necessary, gentle heating and stirring and/or mixing can be employed to effect dissolution of the polymer into the solvent, for example about 12 hours in a water bath at about 60° C. The term polymer is intended to include a product of a polymerization reaction inclusive of homopolymers, copolymers, terpolymers, etc., whether natural or synthetic, including random, alternating, block, graft, crosslinked, blends, compositions of blends and variations thereof. The polymer may be in true solution or saturated in the blended composition. The polymer may also be suspended as particles or supersaturated in the composition. In applications using nozzle 26 having a small diameter orifice 28 for applying composition 10 to prosthesis 12, small polymer particles are to be suspended. Large coagulated polymeric particles, for example larger than the diameter of orifice 28, can clog nozzle 26. Supersaturation of the polymer can adversely affect the flow of composition 10 through nozzle 26 having a small diameter orifice 28 which can result in nonuniformity of the coating on prosthesis 12.

The polymer should be biocompatible, for example a polymeric material which, in the amounts employed, is non-toxic and chemically inert as well as substantially non-immunogenic and non-inflammatory. Suitable polymeric materials can include, but are not limited to, polycaprolactone (PCL), poly-D,L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly(amino acids), cyanoacrylates, poly(trimethylene carbonate), poly(iminocarbonate), copoly(ether-esters), polyalkylene oxalates, polyphosphazenes, polyiminocarbonates, and aliphatic polycarbonates, fibrin, fibrinogen, cellulose, starch, collagen, Parylene®, Parylast®, polyurethane, polyethylene, polyethylene teraphthalate, ethylene vinyl acetate, ethylene vinyl alcohol, silicone, polyethylene oxide, polybutylene terepthalate (PBT)-co-PEG, PCL-co-PEG, PLA-co-PEG, polyacrylates, polyoxaesters, polyvinyl pyrrolidone (PVP), polyacrylamide (PAAm), and combinations thereof.

The solvent can be any single solvent or a combination of solvents capable of dissolving the polymer. The particular solvent or combination of solvents selected is dependent on factors such as the material from which prosthesis 12 is made and the particular polymer selected. Representative examples of suitable solvents include aliphatic hydrocarbons, aromatic hydrocarbons, alcohols, ketones, dimethyl sulfoxide (DMSO), tetrahydrofuran (THF), dihydrofaran (DHF), dimethylacetamide (DMAC), acetates and combinations thereof.

Typically, the polymer can include from about 0.1% to about 25% by weight of the total weight of composition 10. Typically, the solvent can include from about 75% to about 99.9% by weight of the total weight of composition 10. A specific weight ratio is dependent on factors such as the material from which prosthesis 12 is made, the geometrical structure of prosthesis 12, the particular polymer or combination of polymers selected, the particular solvent or combination of solvents selected, and the solubility of the selected polymer(s) in the selected solvent(s).

In accordance with another embodiment, sufficient amounts of a therapeutic substance or a combination of substances are dispersed in the blended composition of the polymer and the solvent. In this embodiment, the polymer can include from about 0.1% to about 25% by weight of the total weight of composition 10, the solvent can include from about 49.9% to about 99.8% by weight of the total weight of composition, and the therapeutic substance can include from about 0.1% to about 50% by weight of the total weight of composition 10. Selection of a specific weight ratio of the polymer and the solvent is dependent on factors such as the material from which prosthesis 12 is made, the geometrical structure of prosthesis 12, the particular polymer or combination of polymers selected, the particular solvent or combination of solvents selected, the solubility of the selected polymer(s) in the selected solvent(s), and the type and amount of therapeutic substance employed.

The particular weight percentage of a therapeutic substance mixed within composition 10 depends on factors such as the type of therapeutic substance selected, the solubility of the selected therapeutic substance, the duration of the release, the cumulative amount of release, and the release rate that is desired. The therapeutic substance should be in true solution, saturated, supersaturated, or in fine, suspended particles in the blended composition 10. If the therapeutic substance is not completely soluble in composition 10, operations including gentle heating, mixing, stirring, and/or agitation can be employed to effect homogeneity of the residues. In applications using nozzle 26 having a small diameter orifice 28 through which composition 10 is applied to prosthesis 12, the therapeutic substance is to be suspended in small particles. Large coagulated therapeutic particles, for example larger than the diameter of orifice 28, clog nozzle 26. Supersaturation of the therapeutic substance can adversely affect the flow of composition 10 through nozzle 26 having a small diameter orifice 28 which can result in non-uniformity of the coating on prosthesis 12.

Exposure of composition 10 to the therapeutic substance is not permitted to adversely alter the therapeutic substance's composition or characteristic. Accordingly, the particular therapeutic substance is selected for mutual compatibility with composition 10. Therapeutic substances or agents may include, but are not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyriridine (a PDGF antagonist), and nitric oxide. An example of an antiallergic agent is permirolast potassium. Other therapeutic substances or agents which may be appropriate include alpha-interferon, genetically engineered epithelial cells, and dexamethasone. While the foregoing therapeutic substances or agents are well known for their preventative and treatment properties, the substances or agents are provided by way of example and are not meant to be limiting. Other therapeutic substances which are currently available or may be developed are equally applicable for use with the present invention. The treatment of patients using the above mentioned medicines is well known to those of ordinary skill in the art.

In another embodiment, composition 10 is a polymer or combination of polymers without a solvent. Because polymers are typically in solid form at room temperature, composition 10 may be heated prior to deposition onto prosthesis 12. Composition 10 may also include a therapeutic substance. In embodiments including a therapeutic substance as well as polymeric material, the polymer can include from about 50% to about 99.9% by weight of the total weight of composition 10 and the therapeutic substance can include from about 0.1% to about 50% by weight of the total weight of composition 10. Selection of a specific weight ratio is dependent on factors such as the material from which prosthesis 12 is made, the geometrical structure of prosthesis 12, and the particular polymer or combination of polymers selected as well as the type and amount of therapeutic substance employed, the duration of the release, the cumulative amount of the release, and the release rate that is desired. Exposure of composition 10 to the therapeutic substance is not permitted to adversely alter the therapeutic substance's composition or characteristic. Accordingly, the particular therapeutic substance is selected for compatibility with the polymer. In addition, heat applied to composition 10, such as heat employed to liquify an otherwise solid polymer prior to deposition onto prosthesis 12, may not adversely alter the therapeutic substance's composition or characteristic.

In still another embodiment, composition 10 constitutes a monomer or combination of monomers. Composition 10 may also include a solvent. Following application of composition 10 to prosthesis 12, the monomeric composition 10 is cured to form a polymeric coating. Curing may be accomplished photochemically using ultraviolet or visible irradiation and a photoinitiator, thermally, or by moisture curing at room temperature. The practice of these and other suitable curing procedures are well known to one of ordinary skill in the art. In embodiments including a solvent as well as monomeric material, the monomer constitutes from about 0.1% to about 50% by weight of the total weight of composition 10 and the solvent constitutes from about 50% to about 99.9% by weight of the total weight of composition 10. Composition 10 may also include a therapeutic substance. In embodiments including a monomer and a therapeutic substance but no solvent, the monomer can include from about 50% to about 99.9% by weight of the total weight of composition 10 and the therapeutic substance can include from about 0.1% to about 50% by weight of the total weight of composition 10. In embodiments including a solvent as well as monomeric material and a therapeutic substance, the monomer constitutes from about 0.1% to about 49.9% by weight of the total weight of the composition, the solvent constitutes from about 49.9% to about 99.8% by weight of the total weight of said composition, and the therapeutic substance constitutes from about 0.1% to about 50% by weight of the total weight of the composition. Selection of a specific weight ratio is dependent on factors such as the material from which prosthesis 12 is made, the geometrical structure of prosthesis 12, and the particular monomer or combination of monomers selected as well as the type and amount of therapeutic substance employed, the duration of the release, the cumulative amount of the release, and the release rate that is desired. Exposure of composition 10 to the therapeutic substance is not permitted to adversely alter the therapeutic substance's composition or characteristic. Accordingly, the particular therapeutic substance is selected for compatibility with the monomer. In addition, curing the monomer may not adversely alter the therapeutic substance's composition or characteristic.

In another embodiment, composition 10 includes a therapeutic substance without a polymer. Composition 10 may also include a solvent. In embodiments including a solvent as well as a therapeutic substance, the solvent can include from about 50% to about 99.9% by weight of the total weight of composition 10 and the therapeutic substance can include from about 0.1% to about 50% by weight of the total weight of composition 10. Selection of a specific weight ratio is dependent on factors such as the material from which prosthesis 12 is made, the geometrical structure of prosthesis 12, and the particular solvent or combination of solvents selected as well as the type and amount of therapeutic substance employed, the duration of the release, the cumulative amount of the release, and the release rate that is desired. Exposure of the solvent to the therapeutic substance is not permitted to adversely alter the substance's composition or characteristic. Accordingly, the particular therapeutic substance is selected for compatibility with the solvent.

A Method for Coating a Prosthesis

To form a coating onto a surface of prosthesis 12, the surface of prosthesis 12 should be clean and free from contaminants that may be introduced during manufacturing. However, the surface of prosthesis 12 requires no particular surface treatment to retain the applied coating.

Figure 6A:
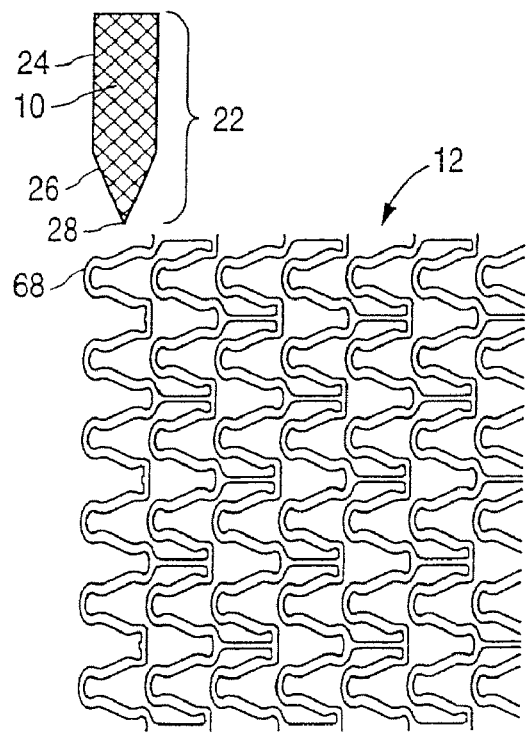
FIG. 6A illustrates a magnified view of a surface of a prosthesis in relation to a nozzle of a dispenser assembly containing a composition.

In one set of embodiments, holder assembly 14 moves along a predetermined path while dispenser assembly 22 remains stationary during deposition of composition 10. In these embodiments, nozzle 26 of dispenser assembly 22 is positioned at a load position over, or in contact with, a strut 68 of prosthesis 12 as shown in FIG. 6A. As composition 10 is deposited, dispenser assembly 22 remains stationary while prosthesis 12 in holder assembly 14 is moved via holder motion control system 16 along a pre-determined path beneath the stationary nozzle 26, thereby causing composition 10 to be deposited in a preselected geometrical pattern on prosthesis 12.

In another set of embodiments, dispenser assembly 22 moves along a predetermined path while holder assembly 14 remains stationary during deposition of composition 10. In such embodiments, nozzle 26 of dispenser assembly 22 is positioned at a load position over, or in contact with, strut 68 of prosthesis 12 as shown in FIG. 6A. As composition 10 is deposited, holder assembly 14 remains stationary while dispenser assembly 22 is moved via dispenser motion control system 32 along a pre-determined path around the stationary prosthesis 12, thereby causing the composition 10 to be deposited in a preselected geometrical pattern on prosthesis 12.

In still another set of embodiments, both dispenser assembly 22 and holder assembly 14 move along respective predetermined paths during deposition of composition 10. By example and not limitation, dispenser assembly 22 may move in the x, y, and z directions while holder assembly 14 may move rotationally. In these embodiments, nozzle 26 of dispenser assembly 22 is positioned at a load position over, or in contact with, strut 68 of prosthesis 12 as shown in FIG. 6A. As composition 10 is deposited, holder assembly 14 is moved via holder motion control system 16 along a pre-determined path while dispenser assembly 22 is moved via dispenser motion control system 32 along another pre-determined path, thereby causing composition 10 to be deposited in a preselected geometrical pattern on prosthesis 12.

Figure 6B:
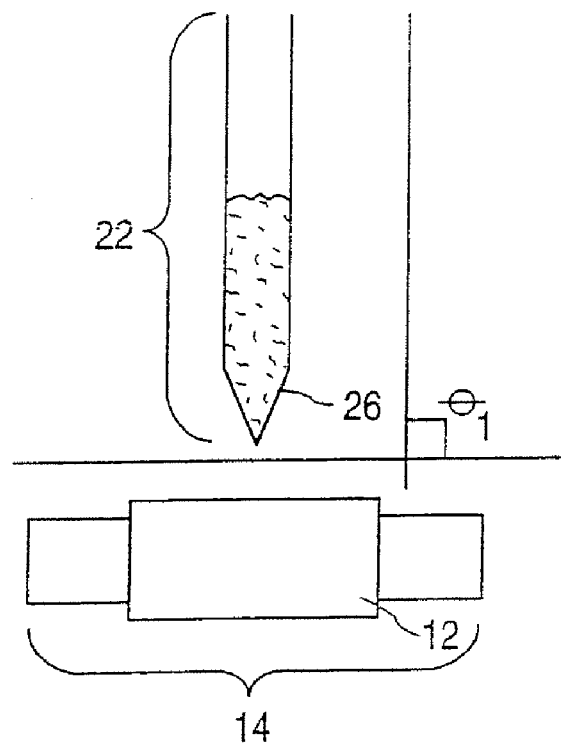
FIG. 6B illustrates a dispenser assembly having a nozzle positioned at a 90° angle $\theta_1$ with respect to the prosthesis during deposition.
Figure 6C:
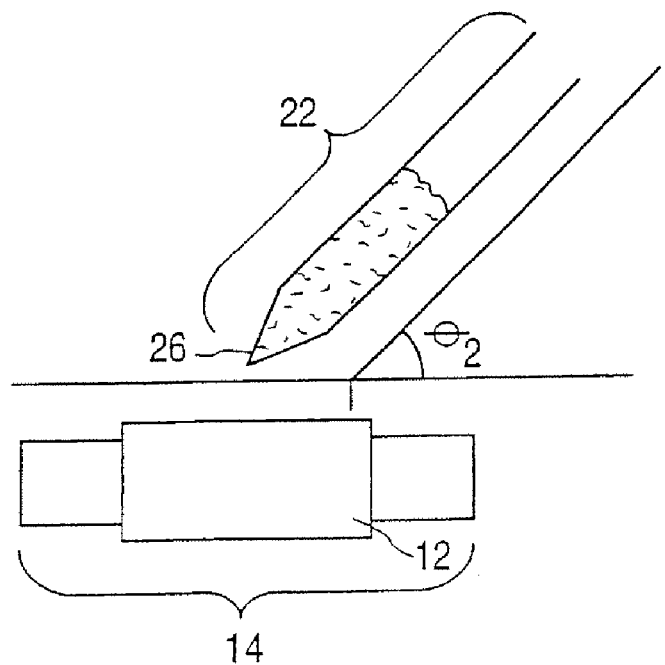
FIG. 6C illustrates a dispenser assembly having a nozzle positioned at an angle $\theta_2$ that is less than 90° with respect to the prosthesis during deposition.

As depicted in FIG. 6B, nozzle 26 may be positioned at an angle $\theta_1$ of about 90° with respect to prosthesis 12 during deposition of composition 10. Alternatively, nozzle 26 may be positioned at an angle $\theta_2$ of less than 90° with respect to prosthesis 12 during deposition of composition 10 as depicted in FIG. 6C.

Figure 7A:
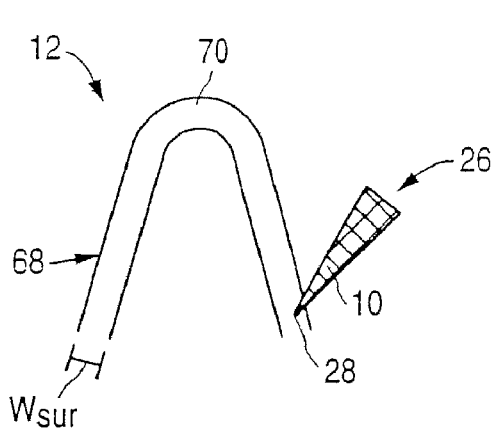
FIGS. 7A and 7B illustrate the application of the composition to a surface of a prosthesis.
Figure 7B:
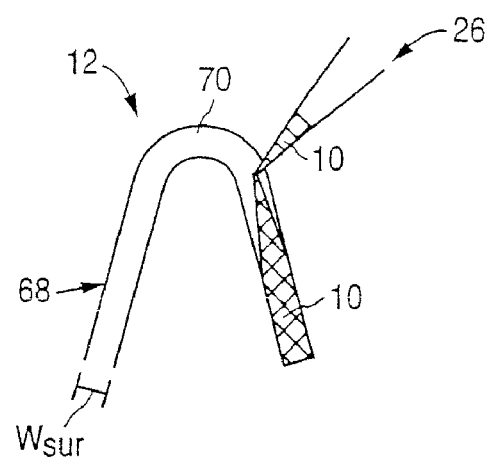
Figure 8A:
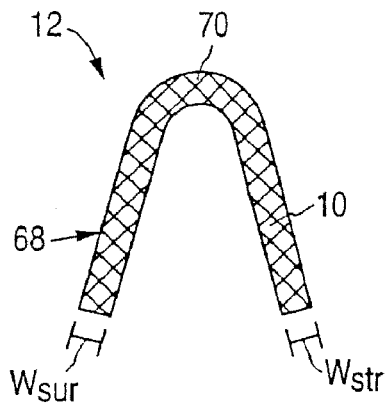
FIG. 8A illustrates a strut having a coating that completely covers a surface.
Figure 8B:
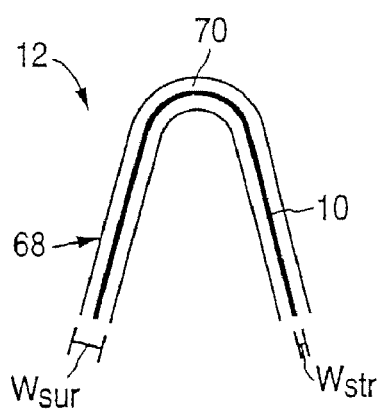
FIG. 8B illustrates a strut having a continuous stream of coating that is in a straight line.
Figure 8C:
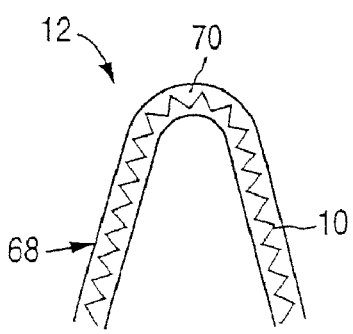
FIG. 8C illustrates a strut having a continuous stream of coating that is in an angular line.
Figure 8D:
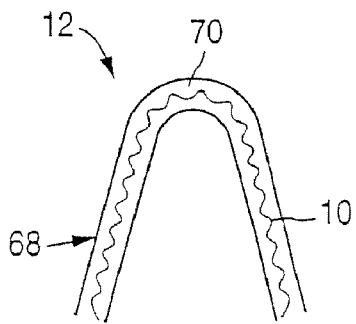
FIG. 8D illustrates a strut having a continuous stream of coating that is formed in a curved line.

Composition 10 maybe applied along struts 68 of prosthesis 12 in a variety of deposition patterns and having a variety of thicknesses. FIGS. 7A-7B illustrate the deposition of composition 10 along a surface 70 having a surface width $w_{sur}$ in accordance with one set of embodiments of the method. In FIG. 7A, nozzle 26 containing composition 10 is positioned over, or in contact with, strut 68 of prosthesis 12. In FIG. 7B, the deposition of composition 10 in a preselected geometrical pattern continues along surface 70 of prosthesis 12. When deposition onto strut 68 of prosthesis 12 is complete, a continuous stream of composition 10 having a selected stream width $w_{str}$ may follow at least a portion of surface 70 of prosthesis 12. The stream width $w_{str}$ may, for example, be equal to or larger than the surface width $w_{sur}$ such that the continuous stream covers surface 70 completely as depicted in FIG. 8A. Alternatively, the stream width $w_{str}$ may be smaller than the surface width $w_{sur}$ such that the continuous stream partially covers a portion of surface 70 in a straight line as depicted in FIG. 8B, in an angular line as depicted in FIG. 8C, or in a curved line as depicted in FIG. 8D. The resulting preselected geometrical pattern of composition 10 may be repeated on a single strut 68 or on more than one strut 68 of prosthesis 12.

Figure 8E:
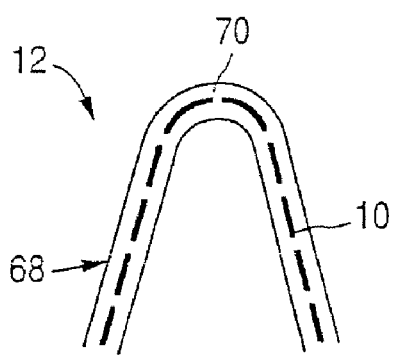
FIG. 8E illustrates a strut having an intermittent pattern of coating that is in a straight line.
Figure 8F:
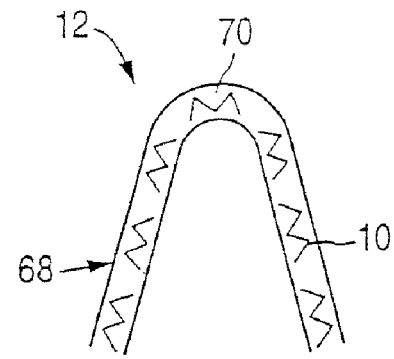
FIG. 8F illustrates an example of a strut having an intermittent pattern of coating that is applied in an angular line.
Figure 8G:
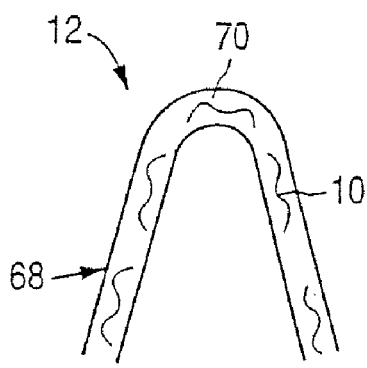
FIG. 8G illustrates an example of a strut having an intermittent pattern of coating that is applied in a curved line.
Figure 8H:
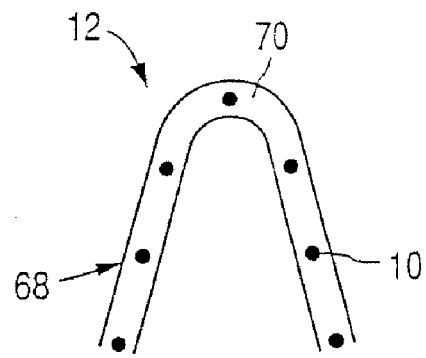
FIG. 8H illustrates a strut having an intermittent pattern of coating which includes beads.
Figure 8I:
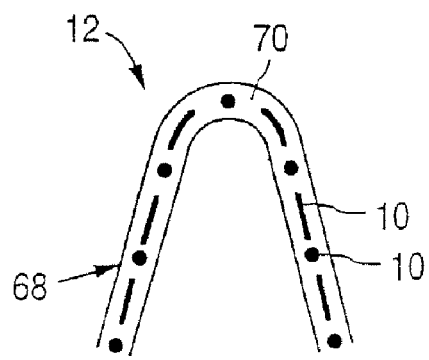
FIG. 8I illustrates a strut having an intermittent pattern of coating which includes beads and straight line streams.

In an alternative set of embodiments, composition 10 may be deposited in an intermittent pattern along at least a portion of surface 70 of prosthesis 12. Delivery of an intermittent pattern may be achieved where delivery is started and stopped at predetermined intervals to yield patterns that are in a straight line as depicted in FIG. 8E, patterns that are in an angular line as depicted in FIG. 8F, patterns that are in a curved line as depicted in FIG. 8G, patterns that include at least one bead along surface 70 of prosthesis 12 as depicted in FIG. 8H, or combinations thereof as depicted in FIG. 8I. The resulting preselected geometrical pattern of composition 10 maybe repeated on a single strut 68 or on more than one strut 68 of prosthesis 12.

In another set of embodiments, prosthesis 12 includes a channel 72 having a channel width $w_{chn}$ and extending from a first position 74 to a second position 76 on strut 68 as shown in FIGS. 9A-9B. In FIG. 9A, nozzle 26 containing composition 10 is positioned over, or in contact with, channel 72. In FIG. 9B, the deposition of composition 10 in a preselected geometrical pattern continues at least partially along channel 72. When deposition into channel 72 is complete, a continuous stream of composition 10 having a selected stream width $w_{str}$ may fill at least a portion of channel 72. The stream width $w_{str}$ may, for example, be equal to or larger than channel width $w_{chn}$ such that channel 72 is filled completely as depicted in FIG. 10A. Alternatively, the stream width $w_{str}$ may be smaller than the channel width $w_{chn}$ so as to partially fill channel 72 with a continuous stream that is substantially in a straight line as depicted in FIG. 10B, in an angular line as depicted in FIG. 10C, or in a curved line as depicted in FIG. 10D. The resulting preselected geometrical pattern of composition 10 may be repeated on a single strut 68 or on more than one strut 68 of prosthesis 12.

Figure 10E:
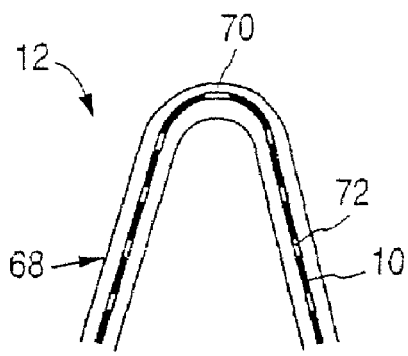
FIG. 10E illustrates a strut having an intermittent pattern of coating that is in a straight line in a channel within the strut.
Figure 10F:
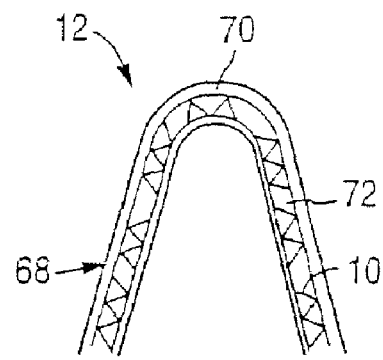
FIG. 10F illustrates a strut having an intermittent pattern of coating that is applied in an angular line in a channel within the strut.
Figure 10G:
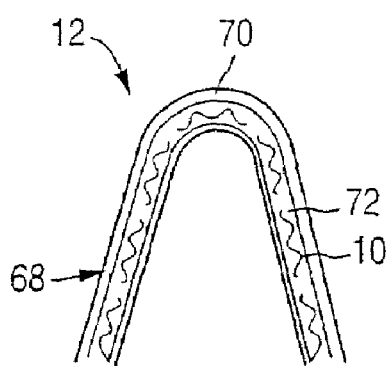
FIG. 10G illustrates a strut having an intermittent pattern of coating that is applied in a curved line in a channel within the strut.
Figure 10H:
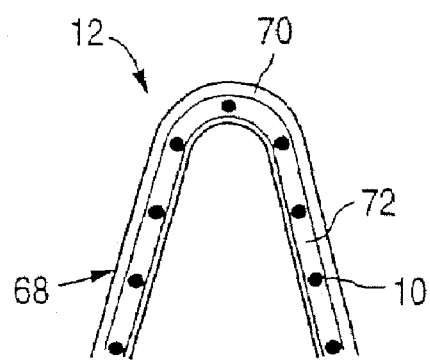
FIG. 10H illustrates a strut having an intermittent pattern of coating that includes beads in a channel within the strut.
Figure 10I:
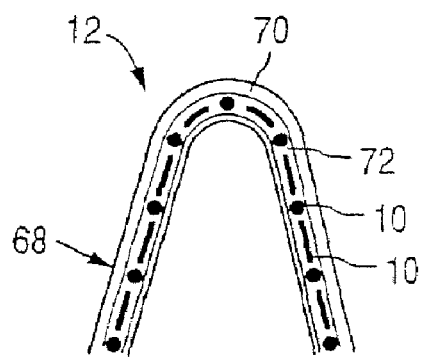
FIG. 10I illustrates a strut having an intermittent pattern of coating that includes beads and straight line streams in a channel within the strut.

In an alternative set of embodiments, deposition of an intermittent pattern of composition 10 may be achieved where delivery is started and stopped at predetermined intervals. Resulting patterns at least partially within channel 72 may be in a straight line as depicted in FIG. 10E, in an angular line as depicted in FIG. 10F, in a curved line as depicted in FIG. 10G, include at least one bead as depicted in FIG. 10H, or a combination thereof as depicted in FIG. 10I. The resulting preselected geometrical pattern of composition 10 may be repeated on a single strut 68 or on more than one strut 68 of prosthesis 12.

Figure 11A:
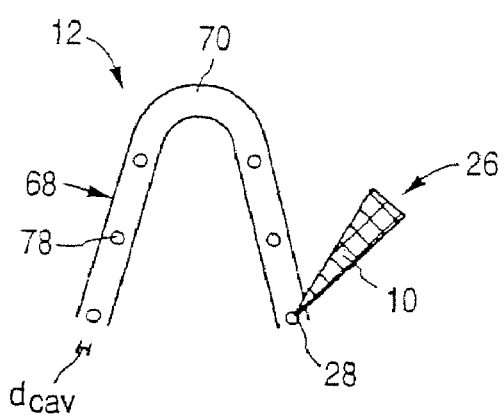
FIGS. 11A and 11B illustrate application of the composition into cavities within a strut.
Figure 11B:
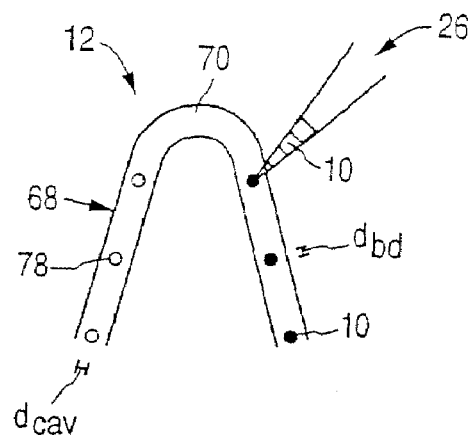
Figure 12A:
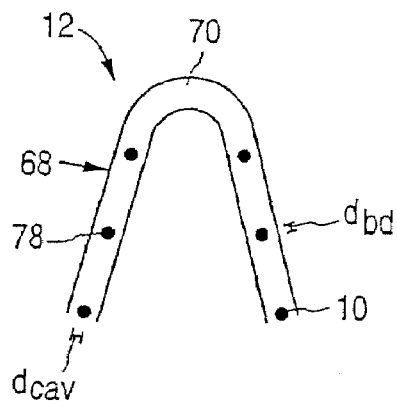
FIG. 12A illustrates a strut having a pattern of coating in which each cavity is filled.
Figure 12B:
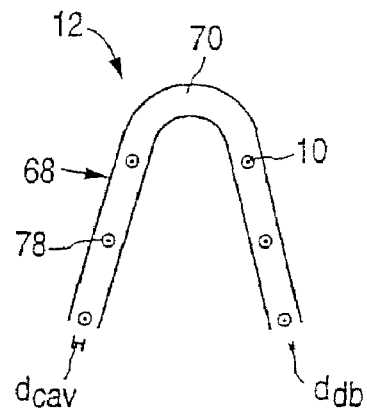
FIG. 12B illustrates a strut having a pattern of coating in which each cavity is partially filled.
Figure 12C:
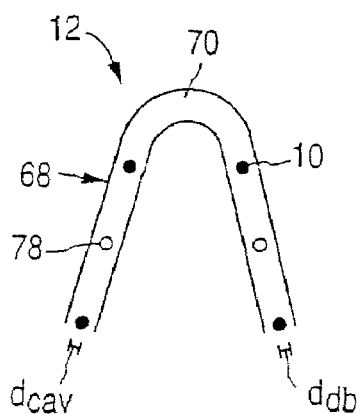
FIG. 12C illustrates a strut having a pattern of coating in which some but not all cavities are filled.
Figure 12D:
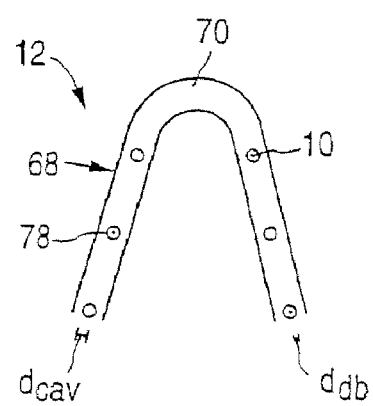
FIG. 12D illustrates a strut having a pattern of coating in which some but not all cavities are partially filled.

In still another set of embodiments, composition 10 is applied into cavities 78 within surface 70 of prosthesis 12 having a cavity diameter $d_{cav}$ as depicted in FIGS. 11A-11B. In FIG. 11A, nozzle 26 containing composition 10 is positioned over, or in contact with, cavity 78 within strut 68 of prosthesis 12. Cavity 78 may be loaded with composition 10 in a preselected geometrical pattern such as, but not limited to, a bead having a selected bead diameter $d_{bd}$. The selected bead diameter $d_{bd}$ may be equal to, larger than or smaller than cavity diameter $d_{cav}$. The filling process may continue as shown in FIG. 11B until a preselected number and geometrical pattern of cavities 78 within prosthesis 12 have been at least partially filled with composition 10. FIG. 12A depicts a deposition pattern in which every cavity 78 is completely filled with composition 10. FIG. 12B depicts a deposition pattern in which every cavity 78 is partially filled with composition 10. Alternatively, composition 10 may be deposited in any number of patterns in which some, but not all, cavities 78 within prosthesis 12 are at least partially filled, as depicted in FIGS. 12C and 12D. The resulting preselected geometrical pattern of composition 10 maybe repeated on a single strut 68 or on more than one strut 68 of prosthesis 12.

In some embodiments, prosthesis 12 may be exposed to a drying or curing procedure following the deposition of composition 10 onto prosthesis 12. In embodiments in which composition 10 includes a solvent, for example, the solvent may be removed from composition 10 on prosthesis 12 by allowing the solvent to evaporate. The evaporation can be induced by heating prosthesis 12 at a predetermined temperature for a predetermined period of time. For example, prosthesis 12 can be heated at a temperature of about 60° C. to about 70° C. for about 2 hours to about 24 hours. The heating can be conducted in an anhydrous atmosphere and at ambient pressure. The heating can be conducted under a vacuum condition. Alternatively, an extraction solvent may be employed to remove the solvent from composition 10 on prosthesis 12 so long as the extraction solvent is mutually compatible with the polymer and with the therapeutic substance and does not adversely affect the coating. The use of an extraction solvent in this manner is well known to those of ordinary skill in the art who understand that essentially all of the solvent will be removed from composition 10 but traces or residues can remain blended with the polymer. Following removal of the solvent, a coating remains on prosthesis 12 or a portion thereof.

In other embodiments, such as, but not limited to, embodiments in which composition 10 includes a monomer, prosthesis 10 is exposed to a curing procedure following application of composition 10 to prosthesis 12. Curing may be accomplished photochemically using ultraviolet or visible irradiation and a photoinitiator, thermally, or by moisture curing at room temperature. The practice of these and other suitable curing procedures are well known to one of ordinary skill in the art. Following the curing procedure, a coating remains on prosthesis 12 or a portion thereof.

In still other embodiments in which a drying or curing procedure is used, heating assembly 52 is employed to facilitate localized heating of composition 10 only in the preselected geometrical pattern in which composition 10 was deposited, rather than heating of the entire prosthesis 12 as in the conventional drying and curing methods described above. In such embodiments, heating nozzle 56 is positioned directly over the initial area in which composition 10 is to be dried or cured. Heat having a temperature ranging from about 35° C. to about 100° C. is then delivered to composition 10 for approximately 0.1 seconds to approximately 5 seconds. The temperature and time should be sufficient to dry or cure composition 10 without degrading the components of composition 10.

As heat is delivered, heating nozzle 56 may remain stationary while prosthesis 12 in holder assembly 14 is moved via holder motion control system 16 along a pre-determined path beneath the stationary heating nozzle 56, thereby causing heat to be delivered following the preselected geometrical pattern of the composition on prosthesis 12. Alternatively, holder assembly 14 remains stationary while heating nozzle 56 is moved via heating motion control system 66 or heating control system 60 along a pre-determined path around the stationary prosthesis 12, thereby causing heat to be delivered following the preselected geometrical pattern of the composition on prosthesis 12. In another embodiment, both heating nozzle 56 and holder assembly 14 may move along respective predetermined paths during delivery of heat, thereby causing heat to be delivered following the preselected geometrical pattern of the composition on prosthesis 12. In still another embodiment, heating nozzle 56 may be moved manually by the user along a predetermined path during delivery of heat, thereby causing heat to be delivered following the preselected geometrical pattern of the composition on prosthesis 12. Following the heating procedure via heating assembly 52, a coating remains on prosthesis 12 or a portion thereof.

Figure 13A:
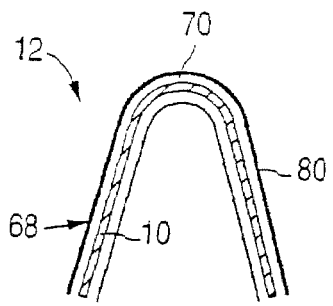
FIG. 13A illustrates a strut having a coating pattern in which a first coating does not make contact with a second coating.
Figure 13B:
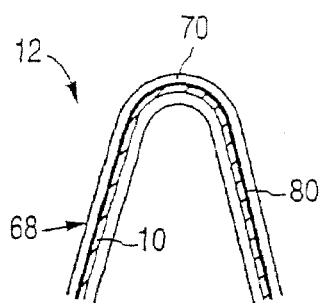
FIGS. 13B and 13C illustrate examples of a strut having a coating pattern in which a first coating makes contact with a second coating.
Figure 13C:
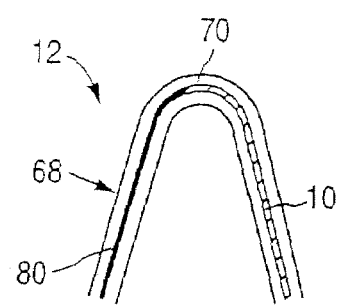

In some embodiments of the method, a second composition 80 can be deposited onto prosthesis 12 concurrent with or subsequent to the application of composition 10 to prosthesis 12. Second composition 80 may differ from first composition 10 in the particular polymer(s) or monomer(s) selected, the concentration of polymer(s) or monomer(s), the particular therapeutic substance(s) selected, the concentration of the therapeutic substance(s), or a combination thereof. Second composition 80 may be deposited to avoid contact with composition 10, as depicted in FIG. 13A. Second composition 80 may also be deposited adjacent to composition 10, as depicted in FIGS. 13B and 13C.

Figure 13D:
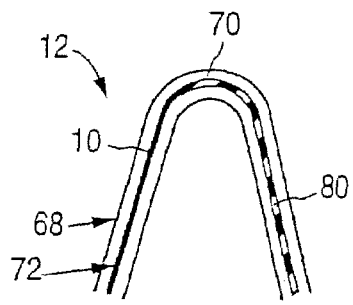
FIG. 13D illustrates a strut having a coating pattern in which a first coating and a second coating are within a channel of the strut.
Figure 13E:
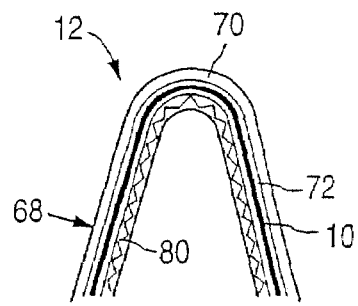
FIG. 13E illustrates a strut having a coating pattern in which a first coating is within a channel of the strut and a second coating is outside the channel of the strut.

In another embodiment in which second composition 80 is employed, first composition 10 and second composition 80 are both deposited within a channel 72 of prosthesis 12, as depicted in FIG. 13D. Alternatively, first composition 10 may be deposited at least partially within channel 72 of prosthesis 12 while second composition 80 is deposited completely outside of channel 72 of prosthesis 12, as depicted in FIG. 13E.

Figure 13F:
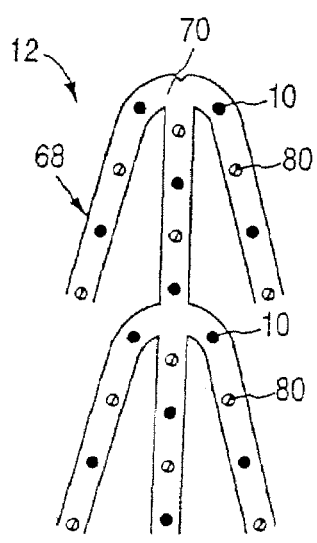
FIG. 13F illustrates a prosthesis having a coating pattern in which cavities having a first coating therein are in the same region of the struts as cavities having a second coating therein.
Figure 13G:
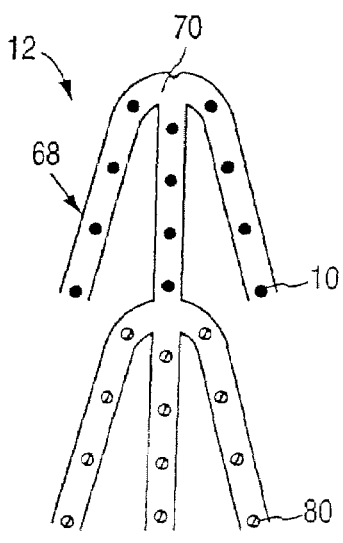
FIG. 13G illustrates a prosthesis having a coating pattern in which cavities having a first coating therein are located in a first strut of the prosthesis and cavities having a second coating therein are located in a different strut of the prosthesis.
Figure 13H:
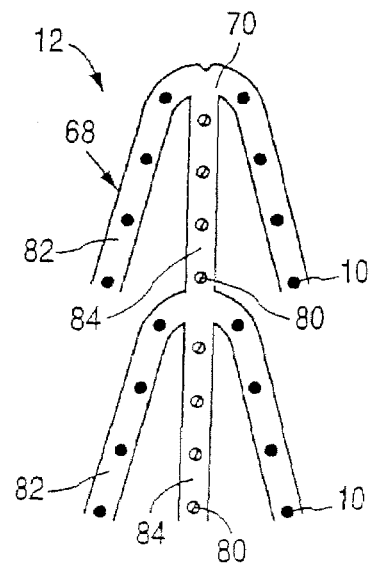
FIG. 13H illustrates a prosthesis having a coating pattern in which cavities having a first coating therein are located in the arms of the struts and cavities having a second coating therein are located in the links of the struts.

In still other embodiments in which second composition 80 is employed, first composition 10 is deposited at least partially within some depots or cavities 78 of prosthesis 12 while second composition 80 is deposited at least partially within other depots or cavities 78 of prosthesis 12. First composition 10 may be deposited in depots or cavities 78 located in the same region as those depots or cavities 78 having second composition 80 deposited therein, as depicted in FIG. 13F. Alternatively, first composition 10 may be deposited in depots or cavities 78 located in a different region than those depots or cavities 78 having second composition 80 deposited therein. By example and not limitation, first composition 10 and second composition 80 may be deposited in depots or cavities 78 located in different struts 68 of prosthesis 12 as depicted in FIG. 13G. Alternatively, first composition 10 may be deposited in depots or cavities 78 within arms 82 of struts 68 while second composition 80 may be deposited in depots or cavities 78 within links 84 of struts 68 as depicted in FIG. 13H.

Figure 14A:
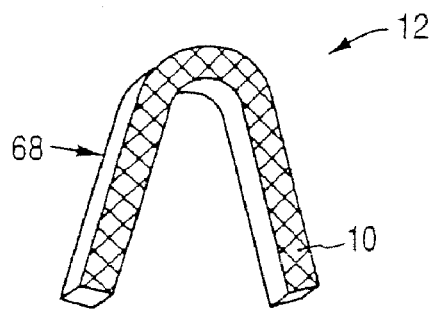
FIGS. 14A and 14B illustrate the coating of a strut with a first coating and a second coating that covers at least a portion of the first coating.
Figure 14B:
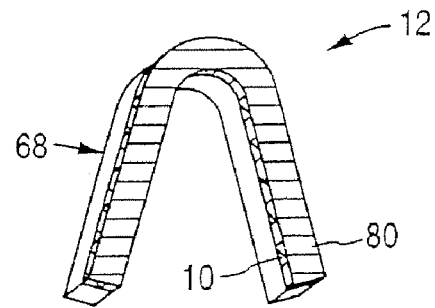
Figure 14C:
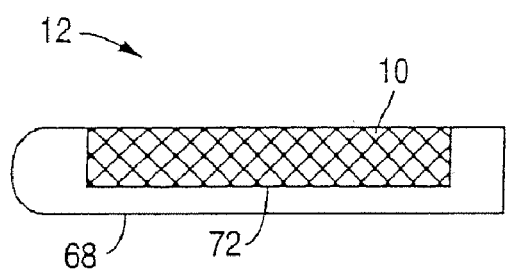
FIGS. 14C and 14D illustrate the coating of a strut with a first coating within a channel and a second coating that covers at least a portion of the first coating within the channel.
Figure 14D:
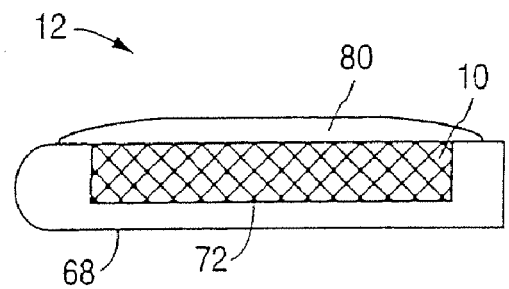
Figure 14E:
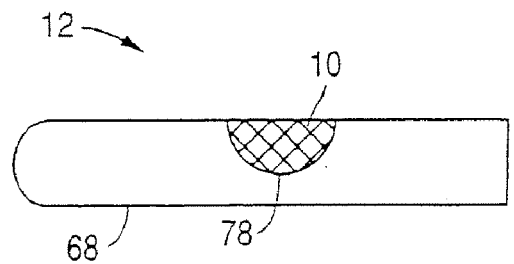
FIGS. 14E and 14F illustrate the coating of a strut with a first coating within a cavity and a second coating that covers at least a portion of the first coating within the cavity.
Figure 14F:
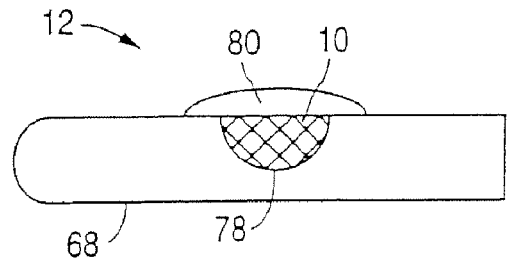

In another set of embodiments in which second composition 80 is employed, second composition 80 is deposited to at least partially cover first composition 10. In one such embodiment, first composition 10 is deposited on prosthesis 12 as shown in FIG. 14A. Second composition 80 is then deposited to at least partially cover first composition 10 as depicted in FIG. 14B. In an alternative embodiment, first composition 10 is deposited within channel 72 of prosthesis 12 as shown in FIG. 14C. Second composition 80 is then deposited to at least partially cover first composition 10 within channel 72 as depicted in FIG. 14D. In still another embodiment, first composition 10 is deposited within at least one depot or cavity 78 of prosthesis 12 as shown in FIG. 14E. Second composition 80 is then deposited to at least partially cover first composition 10 within depot or cavity 78 as depicted in FIG. 14F.

In each of the above-described embodiments in which second composition 80 is deposited to at least partially cover first composition 10, a drying or curing procedure may be employed. The drying or curing procedure may be carried out following the deposition of first composition 10 and prior to the deposition of second composition 80. In other embodiments, the drying or curing procedure may be carried out following the deposition of second composition 80. In still other embodiments, the drying or curing procedure is carried out both after the deposition of first composition 10 and after the deposition of second composition 80. In some embodiments, first composition 10 and/or second composition 80 is dried or cured using procedures that are well known to one of ordinary skill in the art, such as those described above. In an alternative set of embodiments, first composition 10 and/or second composition 80 is dried or cured using heating assembly 52 as described above.

In still other embodiments of the method, composition 10 can be redistributed on prosthesis 12 following the application of composition 10 to prosthesis 12 and prior to any drying or curing procedure. In the embodiments depicted in FIGS. 15A-15D, composition 10 can be redistributed along sides 86 of strut 68. FIG. 15A illustrates strut 68 of prosthesis 12 subsequent to the deposition of composition 10 onto outer surface 88 of strut 68 and prior to the removal of solvent from composition 10. In FIG. 15B, composition 10 is beginning to be redistributed, as evidenced by the flow of composition 10 from outer surface 88 onto sides 86. FIG. 15C illustrates strut 68 on which composition 10 has been redistributed such that composition 10 coats sides 86 as well as outer surface 88 of strut 68. Alternatively, composition 10 can be redistributed such that composition 10 coats sides 86 instead of outer surface 88 upon which composition 10 was originally deposited, as depicted in FIG. 15D. In this alternative embodiment, essentially all of composition 10 will be redistributed from outer surface 88 to sides 86 but traces or residues can remain on outer surface 88.

In another embodiment, composition 10 can be redistributed along an inner surface 90 of prosthesis 12 after composition 10 has been deposited and before the solvent has been removed. FIG. 16A illustrates prosthesis 12 subsequent to the deposition of composition 10 onto outer surface 88. FIG. 16B illustrates prosthesis 12 after composition 10 has been redistributed such that composition 10 coats inner surface 90 as well as outer surface 88 of prosthesis 12. In still another embodiment not depicted, composition 10 can be redistributed along both sides 86 and inner surface 90 of prosthesis 12 after composition 10 has been deposited and before the solvent has been removed.

Redistribution can be accomplished via various techniques including, but not limited to, the use of air pressure, centrifugal force, or a second solvent. Composition 10 can be directed from outer surface 88 of prosthesis 12 onto sides 86 and/or inner surface 90 by passing air across composition 10 on outer surface 88 in bursts or in a steady stream using any method known and available to one of ordinary skill in the art. Spinning prosthesis 12, such as by centrifugation, may cause composition 10 to flow from outer surface 88 onto sides 86 and/or inner surface 90 of prosthesis 12 through centrifugal force. Application of a low viscosity solvent, for example 0.5 to 50 centipoise, to the composition-covered outer surface 88 of prosthesis 12, can reduce the viscosity of composition 10 to readily flow along sides 86 and/or inner surface 90 of prosthesis 12. Following redistribution of composition 10, the solvent(s) may be removed from composition 10 as described above to form a coating on prosthesis 12.

By way of example, and not limitation, the coating formed on prosthesis 12 can have a thickness of about 0.01 microns to about 20 microns. The particular thickness of the coating is dependent on factors such as the desired amount of therapeutic substance, if any, to be incorporated into the coating, the desired use of the coating and the type of procedure for which prosthesis 12 is employed.

Method of Use

In accordance with the above described methods, therapeutic substances can be applied to a prosthesis, for example a stent, retained on the stent during delivery and expansion of the stent, and released at a desired control rate and for a predetermined duration of time at the site of implantation. A stent having the above described medicated coating is useful for a variety of medical procedures, including, by way of example, treatment of obstructions caused by tumors in bile ducts, esophagus, and trachea/bronchi. A stent having the above described medicated coating is particularly useful for treating occluded regions of blood vessels caused by formation of intimal flaps or torn arterial linings, thrombosis, and restenosis. Stents may be placed in a wide array of blood vessels, both arteries and veins. Representative examples of sites include the iliac, renal, and coronary arteries.

Briefly, an angiography is performed to determine the appropriate positioning for stent therapy. Angiography is typically accomplished by injecting a radiopaque contrasting agent through a catheter inserted into an artery or vein as an x-ray is taken. A guidewire is advanced through the lesion or proposed site of treatment. Over the guidewire is passed a delivery catheter which allows a stent in a collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above described coating may be expanded at the desired area of treatment. A post insertion angiogram may also be utilized to confirm appropriate positioning.

While particular embodiments of the present invention have been shown and described, it will be obvious to those having ordinary skill in the art that changes and modifications can be made without departing from this invention in its broader aspects and, therefore, the appended claims are to encompass within their scope all such changes and modifications as fall within the true spirit and scope of this invention.

What is claimed is:

1. A manufacturing method, comprising:
   causing a coating dispenser to be moved, for the application of a coating substance, along a path defined by a pattern of a frame structure of a stent such that the coating dispenser avoids the application of the coating substance in a space between the frame structures; and
   applying the coating substance to the frame structure of the stent.

2. The method of claim 1, additionally including causing the coating dispenser and the stent to be positioned next to or in contact with each other.

3. The method of claim 1, wherein the substance comprises a therapeutic substance.

4. The method of claim 1, wherein the path is between a first position and a second position along a segment of the pattern of the frame structure.

5. The method of claim 1, wherein the stent is maintained in a stationary position.

6. The method of claim 1, wherein the stent is capable of moving independently of the dispenser.

7. The method of claim 1, wherein the dispenser is capable of moving in intervals of less than 0.001 inches.

8. The method of claim 1, wherein the stent is maintained in close proximity to or in contact with the dispenser for the application of the coating substance.

9. The method of claim 1, wherein the dispenser is in communication with a computer for controlling the operation of the dispenser.

10. The method of claim 1, wherein the dispenser is in communication with a means for controlling the delivery of the coating substance out from the dispenser.

11. The method of claim 1, wherein the coating substance is applied on a surface of the frame structure.

12. The method of claim 1, wherein the coating substance comprises a polymer.

13. A manufacturing method, comprising:
    causing a stent to be moved such that the positioning of a dispenser, for the application of a coating substance, is maintained along a path defined by a pattern of a frame structure of the stent such that the dispenser avoids application of the coating substance in a space between the frame structures; and
    applying the coating substance to the frame structure of the stent.

14. The method of claim 13, additionally including causing the stent and the coating dispenser to be positioned next to or in contact with each other.

15. The method of claim 13, wherein the substance comprises a therapeutic substance.

16. The method of claim 13, wherein the path is between a first position and a second position along a segment of the pattern of the frame structure.

17. The method of claim 13, wherein the dispenser is held in a stationary position.

18. The method of claim 13, wherein the dispenser is capable of rotating about the circumference of the stent.

19. The method of claim 13, wherein the dispenser is capable of moving independently of the stent.

20. The method of claim 13, wherein the stent is moved in intervals.

21. The method of claim 13, wherein the stent is capable of being moved in intervals of less than 0.001 inches.

22. The method of claim 13, wherein the stent is maintained in close proximity to or in contact with the dispenser for the application of the coating substance.

23. The method of claim 13, wherein the coating substance is applied on a surface of the frame structure.

24. The method of claim 13, wherein the coating substance comprises a polymer.

25. A manufacturing method, comprising
    causing a coating dispenser to move along a framework of a stent from a first position to a second position by a means including operation of a computer for depositing a coating material on the framework of the stent wherein the movement of the dispenser from the first position to the second position is dictated by a pattern of the framework of the stent such that the dispenser is moved along a pathway of the pattern of the framework between the first position and the second position; and
    applying the coating substance to the framework of the stent.

26. The method of claim 25, additionally comprising causing the stent to move for adjusting the position of the stent with respect to the dispenser.

27. The method of claim 25, additionally comprising causing the stent to move in concert with the dispenser so as to maintain the dispenser within the pathway of the pattern of the framework.

28. The method of claim 25, wherein the pathway between the first position and the second position includes a bend or a curvature.

29. The method of claim 25, where the dispenser is in contact with the stent during movement along the pathway.

30. The method of claim 25, wherein the dispenser does not make contact with the stent during movement along the pathway.

31. The method of claim 25, wherein the coating material includes a polymer and/or a drug.

32. The method of claim 25, additionally comprising causing the stent to move so as to position or maintain the dispenser next to or in contact with the stent.

33. A manufacturing method, comprising
causing a stent to move from a first position to a second position by a means including operation of a computer such that the positioning of a dispenser, for application of a coating substance, is maintained along a framework of the stent and when the stent is moved the dispenser stays within a pathway of a pattern of the framework between the first position and the second position; and
applying the coating substance to the framework of the stent.

34. The method of claim 33, additionally comprising causing the dispenser to move for adjusting the position of the dispenser with respect to the stent.

35. The method of claim 33, additionally comprising causing the dispenser to move in concert with the stent so as to maintain the dispenser within the pathway of the pattern of the framework.

36. The method of claim 33, wherein the pathway between the first position and the second position includes a bend or a curvature.

37. The method of claim 33, where the dispenser is in contact with the stent during movement along the pathway.

38. The method of claim 33, wherein the dispenser does not make contact with the stent during movement along the pathway.

39. The method of claim 33, wherein the coating substance includes a polymer and/or a drug.

40. The method of claim 33, additionally comprising causing the dispenser to move so as to position or maintain the stent next to or in contact with the dispenser.

* * * * *